(12) United States Patent
Abbott et al.

(10) Patent No.: US 11,135,027 B2
(45) Date of Patent: Oct. 5, 2021

(54) COMPUTER-ASSISTED TELEOPERATED SURGERY SYSTEMS AND METHODS

(71) Applicant: Intuitive Surgical Operations, Inc., Sunnyvale, CA (US)

(72) Inventors: Ryan Charles Abbott, San Jose, CA (US); Daniel H. Gomez, Los Gatos, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 243 days.

(21) Appl. No.: 16/326,851

(22) PCT Filed: Oct. 4, 2017

(86) PCT No.: PCT/US2017/055130
§ 371 (c)(1),
(2) Date: Feb. 20, 2019

(87) PCT Pub. No.: WO2018/067696
PCT Pub. Date: Apr. 12, 2018

(65) Prior Publication Data
US 2019/0223967 A1 Jul. 25, 2019

Related U.S. Application Data

(60) Provisional application No. 62/404,069, filed on Oct. 4, 2016.

(51) Int. Cl.
*A61B 34/35* (2016.01)
*A61B 17/29* (2006.01)
(Continued)

(52) U.S. Cl.
CPC .............. *A61B 34/35* (2016.02); *A61B 17/29* (2013.01); *A61B 34/00* (2016.02); *A61B 90/50* (2016.02);
(Continued)

(58) Field of Classification Search
CPC ......... A61B 34/35; A61B 34/37; A61B 34/00; A61B 34/10; A61B 2034/101;
(Continued)

(56) References Cited

U.S. PATENT DOCUMENTS

| 5,279,309 A | 1/1994 | Taylor et al. |
| 5,397,323 A | 3/1995 | Taylor et al. |

(Continued)

FOREIGN PATENT DOCUMENTS

| WO | WO-2007045810 A2 | 4/2007 |
| WO | WO-2013026412 A1 | 2/2013 |

(Continued)

OTHER PUBLICATIONS

Yung-ping et al., "A Novel Remote Center-of Motion Parallel manipulator for Minimally Invasive Celiac Surgery", IJRES, vol. 3, No. 8, (Aug. 2015), pp. 15-19. (Year: 2015).*

(Continued)

*Primary Examiner* — Melanie R Tyson
*Assistant Examiner* — Uyen N Vo
(74) *Attorney, Agent, or Firm* — Fish & Richardson P.C.

(57) ABSTRACT

A teleoperated manipulator system includes a manipulator assembly and a tool actuation assembly coupled to the manipulator assembly. The tool actuation assembly inserts a tool, such as a surgical instrument, along an insertion axis and also rotates the tool around the insertion axis. The manipulator assembly includes an arm that rotates with reference to amounting base to rotate the tool around a yaw axis that intersects the insertion axis. A distal portion of the (Continued)

arm defines an arcuate pitch arc, and a center of the pitch arc is coincident with the intersection of the insertion axis and the yaw axis. The tool actuation assembly is driven along the pitch arc to pitch the tool. The manipulator system is optionally a telesurgical system, and the tool is optionally a therapeutic, diagnostic, or imaging surgical instrument.

14 Claims, 16 Drawing Sheets

(51) Int. Cl.
　　*A61B 90/50* (2016.01)
　　*A61B 34/00* (2016.01)
　　*A61B 17/00* (2006.01)
　　*A61B 34/30* (2016.01)
　　*A61B 90/57* (2016.01)

(52) U.S. Cl.
　　CPC ............... *A61B 2017/00477* (2013.01); *A61B 2034/302* (2016.02); *A61B 2034/305* (2016.02); *A61B 2090/571* (2016.02)

(58) Field of Classification Search
　　CPC ... A61B 17/29; A61B 90/50; A61B 2090/571; A61B 2017/00477; A61B 2034/302; A61B 2034/305; A61B 34/70
　　See application file for complete search history.

(56) References Cited

U.S. PATENT DOCUMENTS

| | | | |
|---|---|---|---|
| 6,451,027 | B1 | 9/2002 | Cooper et al. |
| 8,004,229 | B2 * | 8/2011 | Nowlin .................. A61B 90/37 318/568.21 |
| 8,151,661 | B2 | 4/2012 | Schena et al. |
| 9,333,041 | B2 | 5/2016 | Yeung et al. |
| 2007/0173789 | A1 | 7/2007 | Schena |
| 2009/0012534 | A1 | 1/2009 | Madhani et al. |
| 2010/0204713 | A1 | 8/2010 | Ruiz et al. |
| 2011/0213383 | A1 | 9/2011 | Lee et al. |
| 2012/0227531 | A1 * | 9/2012 | Subramanian ..... G02B 23/2476 74/490.01 |
| 2013/0144307 | A1 | 6/2013 | Jeong et al. |
| 2014/0276952 | A1 * | 9/2014 | Hourtash ............... A61B 34/30 606/130 |
| 2016/0235490 | A1 | 8/2016 | Srivastava et al. |
| 2017/0020615 | A1 | 1/2017 | Koenig et al. |
| 2018/0049737 | A1 | 2/2018 | Swayze et al. |

FOREIGN PATENT DOCUMENTS

| | | |
|---|---|---|
| WO | WO-2015175200 A1 | 11/2015 |
| WO | WO-2016043845 A1 | 3/2016 |
| WO | WO-2016064616 A1 | 4/2016 |
| WO | WO-2016090459 A1 | 6/2016 |
| WO | WO-2016144998 A1 | 9/2016 |
| WO | WO-2016183054 A1 | 11/2016 |

OTHER PUBLICATIONS

Yip et al., "A New Robotic Uterine Positioner for Laparoscopic Hysterectomy with Passive Safety Mechanisms: Design and Experiments", IEEE/RSJ, (Oct. 2, 2015), pp. 3185-3294. (Year: 2015).*
Extended European Search Report for Application No. EP17859116.0, dated Apr. 20, 2020, 13 pages.
Roh Se-Gon et al., "Development of the SAIT single-port surgicalaccess robot slave arm based on RCM Mechanism", 2015 37th Annual International Conference of the IEEE Engineering in Medicine and Biology Society (EMBC), IEEE, Aug. 25, 2015 (Aug. 25, 2015), pp. 5285-5290, XP032811360.
Yip H.M., et al., "A New Robotic Uterine Positioner for Laparoscopic Hysterectomy with Passive Safety Mechanisms: Design and Experiments", 2015 IEEE/RSJ International Conference on Intelligent Robots and Systems (IROS), IEEE, Sep. 28, 2015, pp. 3188-3194, XP032832040.
Yun-Ping Zhu et al., "A Novel Remote Center-of Motion Parallel manipulator for Minimally Invasive Celiac Surgery," International Journal of Research in Engineering and Science (IJRES), (Online ISSN (Print, Aug. 1, 2015 (Aug. 1, 2015 ), pp. 2320-9364, XP055683263, Retrieved from the Internet: URL:https://pdfs.semanticscholar.org/467a/f5f2bfc016d2992323eb59ec2cbd37be5d07.pdf.
International Search Report and Written Opinion for Application No. PCT/US2017/051846, dated Jan. 10, 2018, 11 pages.
International Search Report and Written Opinion for Application No. PCT/US2017/055130, dated Jan. 23, 2018, 15 pages.
Long J.A., et al., "Development of Miniaturized Light Endoscopeholder Robot for Laparoscopic Surgery," Journal of Endourology, Aug. 2007, vol. 21 (8), pp. 911-914.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

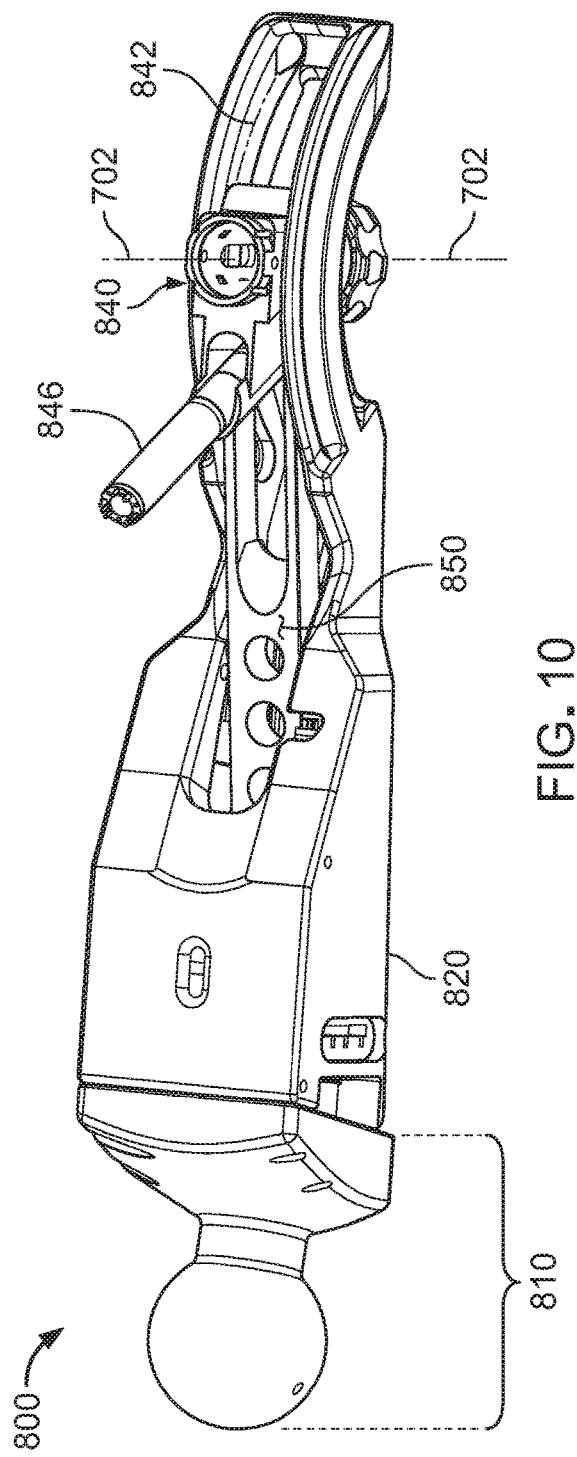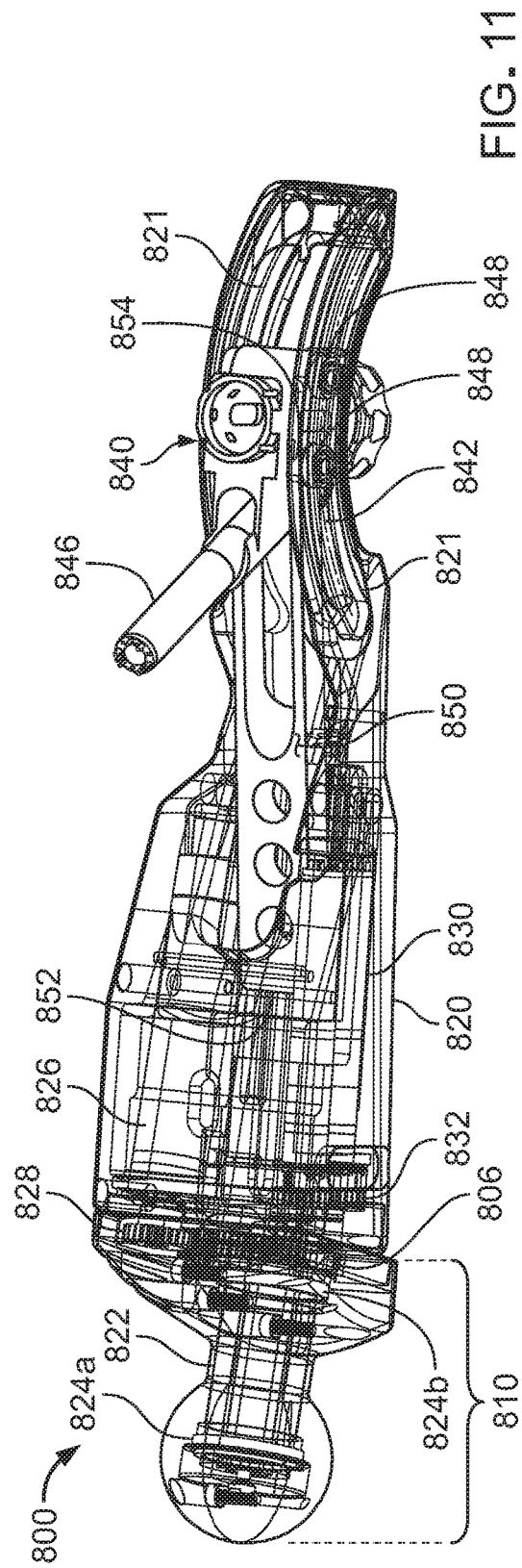

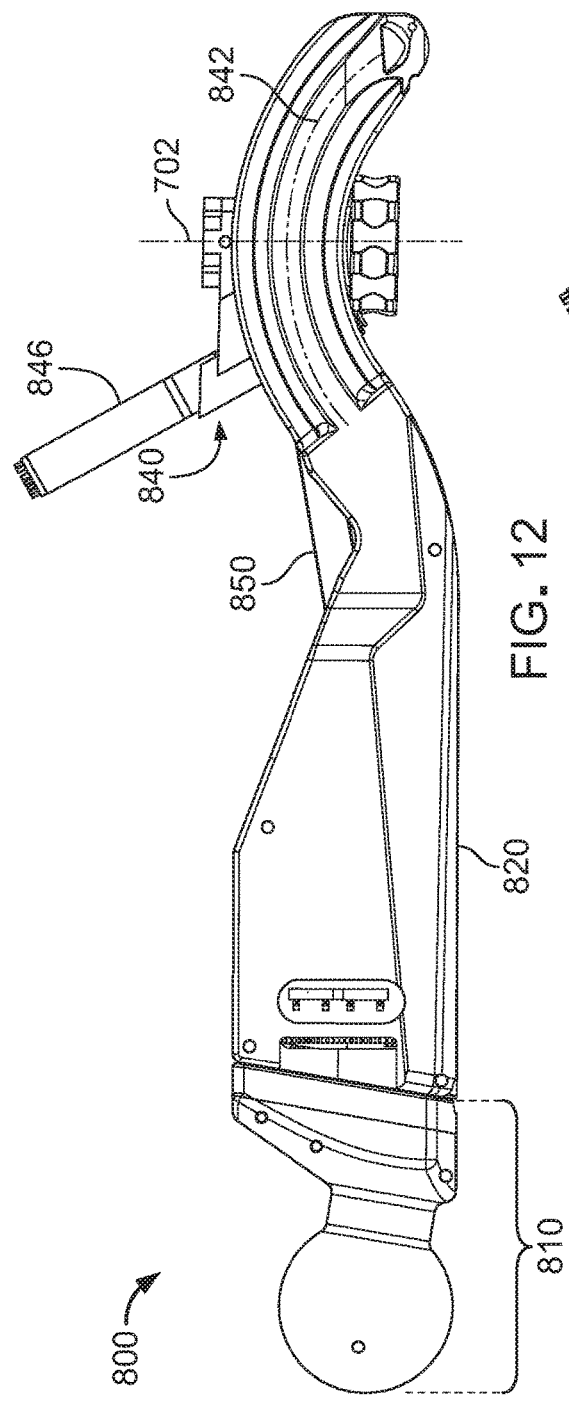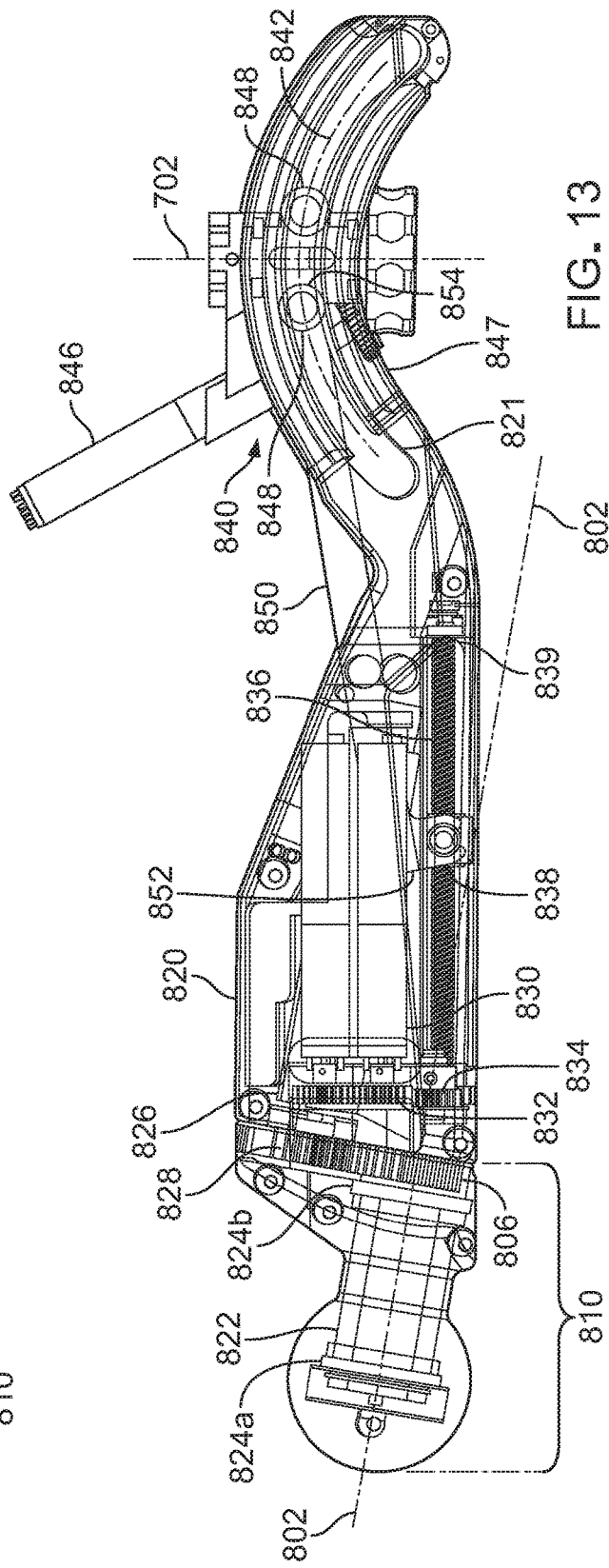

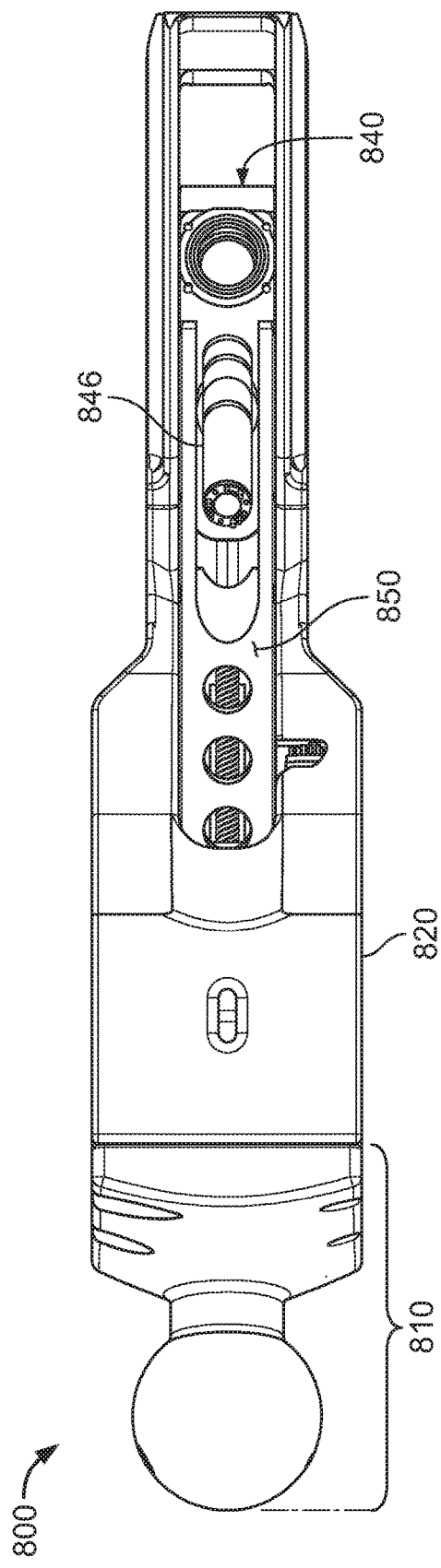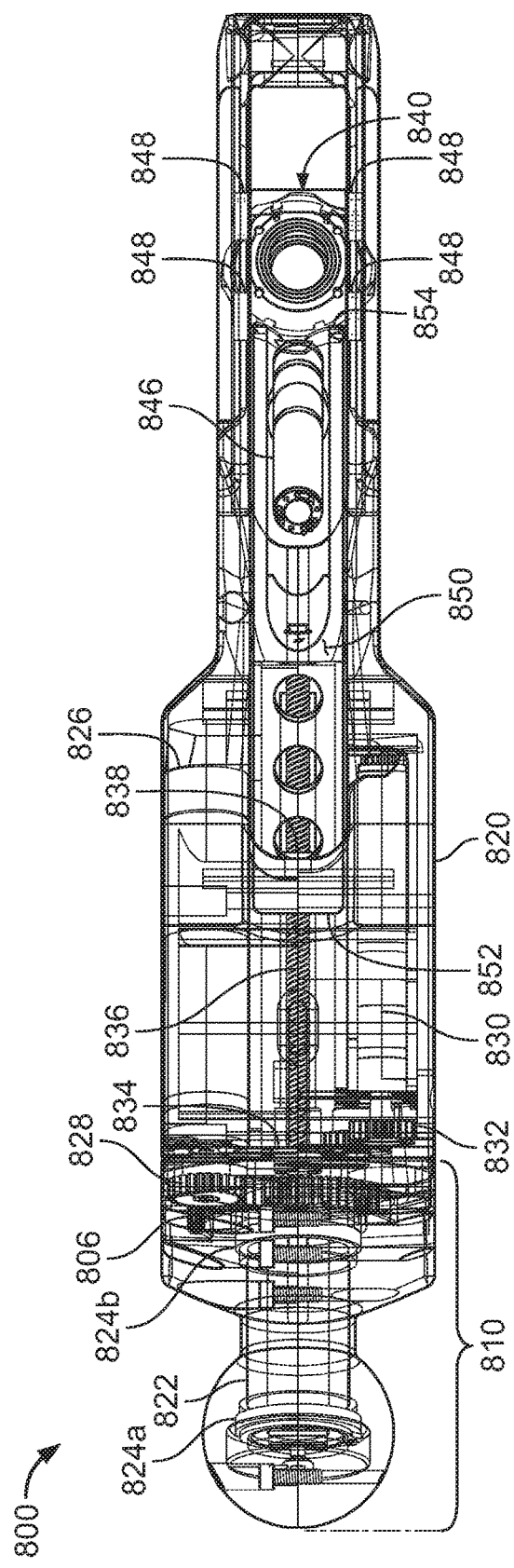

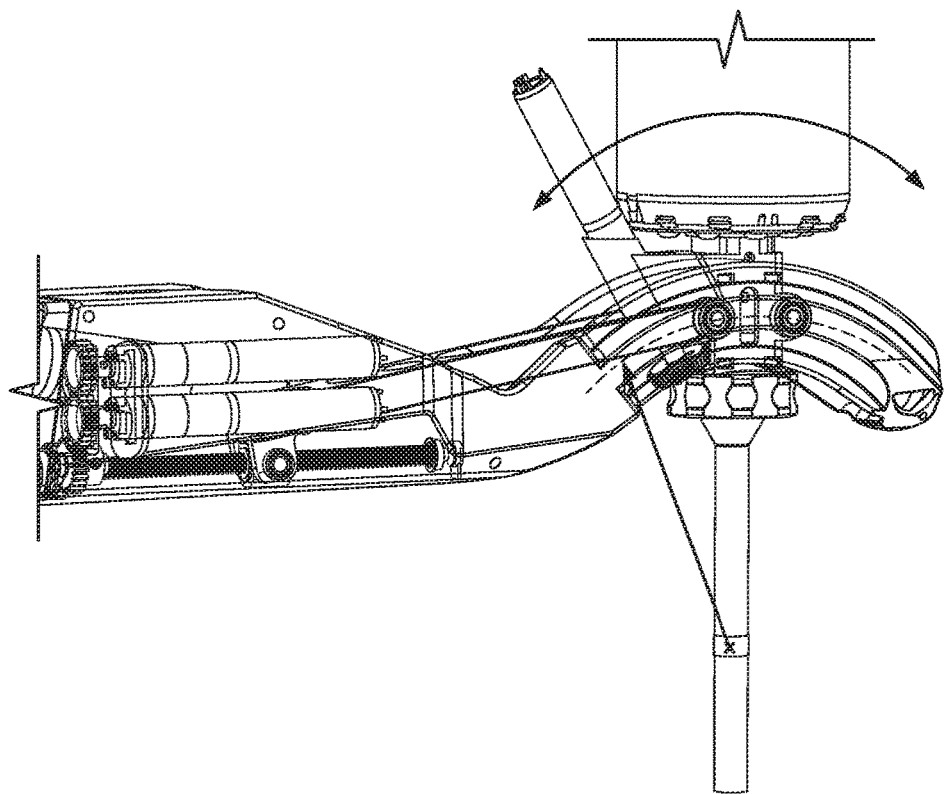
FIG. 18
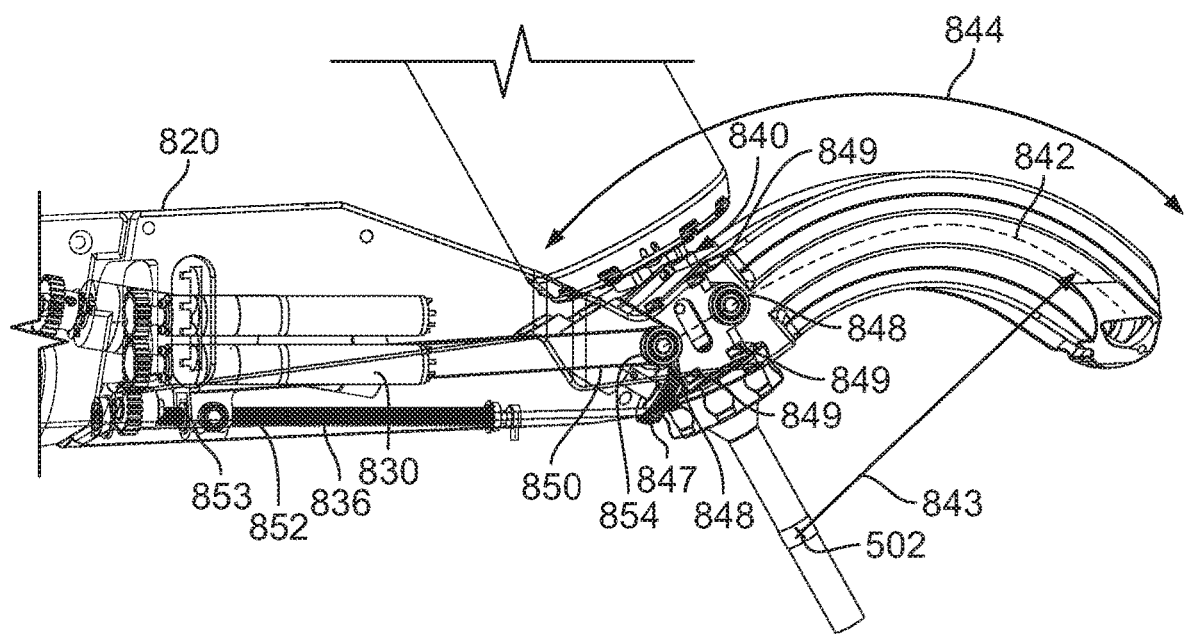

COMPUTER-ASSISTED TELEOPERATED SURGERY SYSTEMS AND METHODS

CROSS-REFERENCE TO RELATED APPLICATIONS

This application is a National Stage Application under 35 U.S.C. § 371 and claims the benefit of International Application No. PCT/US2017/055130, filed Oct. 4, 2017, which claims the benefit of priority to U.S. Provisional Patent Application No. 62/404,069 (filed Oct. 4, 2016), the disclosures of which are incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not Applicable.

BACKGROUND

Teleoperated surgical systems (often called "robotic" surgical systems because of the use of robot technology) and other computer-assisted devices often include one or more tool manipulators to manipulate diagnostic or therapeutic tools for performing a task at a surgical work site and at least one manipulator for supporting an image capturing tool which captures images of the surgical work site. A manipulator arm comprises a plurality of links coupled together by one or more actively controlled joints. In many embodiments, a plurality of actively controlled joints may be provided. The robot arm may also include one or more passive joints, which are not actively controlled, but which comply with movement of an actively controlled joint. Such active and passive joints may be various types, including revolute and prismatic joints. The kinematic pose of the manipulator arm may be determined by the positions of the joints and knowledge of the structure and coupling of the links and the application of known kinematic calculations.

Minimally invasive telesurgical systems for use in surgery are being developed to increase a surgeon's dexterity as well as to allow a surgeon to operate on a patient from a remote location. Telesurgery is a general term for surgical systems in which the surgeon uses some form of remote control, e.g., a servomechanism, or the like, to manipulate surgical tool movements rather than directly holding and moving the tools by hand. In such a telesurgery system, the surgeon is provided with an image of the surgical site at the remote location. While viewing typically a stereoscopic image of the surgical site that provides the illusion of depth on a suitable viewer or display, the surgeon performs the surgical procedures on the patient by manipulating master control input devices, which in turn control the motion of corresponding teleoperated tools. The teleoperated surgical tools can be inserted through small, minimally invasive surgical apertures or natural orifices to treat tissues at surgical sites within the patient, often avoiding the trauma generally associated with accessing a surgical worksite by open surgery techniques. These computer-assisted tele-operated systems can move the working ends (end effectors) of the surgical tools with sufficient dexterity to perform quite intricate surgical tasks, often by pivoting shafts of the tools at the minimally invasive aperture, sliding of the shaft axially through the aperture, rotating of the shaft within the aperture, and the like.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

In one aspect, a teleoperated manipulator system includes a mounting base and an arm attached to the mounting base at a rotational joint. The arm rotates around a yaw axis with reference to the mounting base. A distal portion of the arm defines a pitch arc. A tool actuator assembly is mounted to a tool actuator assembly coupling that translates along the pitch arc. The tool actuation assembly is driven along the pitch arc to move around a center of the pitch arc that is coincident with the yaw axis. The tool actuation assembly inserts a tool along an insertion axis that intersects the yaw axis where the center of the pitch arc is coincident with the yaw axis.

In another aspect, the distal portion of the arm includes a fixed arcuate segment and a movable arcuate segment that telescopes with reference to the fixed arcuate segment. As the tool actuation assembly moves along the pitch arc, the tool actuation assembly coupling moves along the movable arcuate segment, and the movable arcuate segment moves along the fixed arcuate segment.

In further aspects, this disclosure provides devices and methods for minimally invasive robotic surgery using a computer-assisted teleoperated surgery system (a "telesurgical system"). For example, this disclosure provides manipulators for a telesurgical system. In some embodiments, each manipulator includes an arm that is rotatably coupled about a yaw axis to a mounting base that is attachable to a set-up structure. The arm defines an arcuate path along which a tool actuator assembly coupling travels. The tool actuator assembly coupling can receive a surgical tool actuation assembly pod, and it can drive a rotary roll motion of the pod about an insertion axis. In some embodiments, the insertion axis and the yaw axis intersect each other at a point that is coincident with the arcuate path's center point. In some embodiments, a motor-driven link is used to drive the tool actuator coupling along the arcuate path.

In one aspect, this disclosure is directed to a telesurgical manipulator that includes a mounting base configured to releasably couple with a set-up structure of a telesurgical system; an arm rotatably coupled to the mounting base about a yaw axis, the arm defining a pitch arc; an tool actuator assembly coupling defining an insertion axis and configured to releasably couple with a teleoperated tool actuator assembly, the tool actuator coupling translatable along the pitch arc; and a link pivotably coupled to the tool actuator coupling and movably coupled to the arm such that the link is translatable along the arm.

Such a telesurgical manipulator may optionally include one or more of the following features. The insertion axis and the yaw axis may intersect each other at a center of the pitch arc. In some embodiments, at all positions of the tool actuator coupling along the pitch arc, the insertion axis and the yaw axis intersect may each other at a center of the pitch arc. In particular embodiments, at all positions about the yaw axis of the arm relative to the mounting base, the insertion axis and the yaw axis may intersect each other at a center of the pitch arc. In some embodiments, at all positions of the tool actuator assembly coupling along the pitch arc in combination with any position about the yaw axis of the arm relative to the mounting base, the insertion axis and the yaw axis intersect each other at a center of the pitch arc. Translation of the link along the arm causes curvilinear translation of the tool actuator coupling along the pitch arc. The link may be threadably coupled to a lead screw of the arm such that the arm is linearly translatable along the arm by rotation of the lead screw. Translation of the link along the arm causes curvilinear translation of the tool actuator assembly coupling along the pitch arc. The arm may include a pitch-adjustment motor that drives rotation of the lead screw. The tool actuator assembly coupling may include a roll-adjustment motor for rotatably driving a surgical tool actuator assembly about the insertion axis. The tool actuator assembly coupling may be configured to releasably couple with a cannula configured for providing surgical access through a patient's body wall during surgery using the telesurgical manipulator. The arm may include a projection extending into an internal space defined by the mounting base. The projection may define the yaw axis. The mounting base may include a sector gear affixed in a stationary relationship to the mounting base. The arm may include a yaw-adjustment motor that rotatably drives a yaw-adjustment gear meshed with the sector gear. The arm may include a fixed arcuate segment and a movable arcuate segment that is movably coupled with the fixed arcuate segment. The first arcuate segment in combination with the movable arcuate segment may define the pitch arc.

In another aspect, this disclosure is directed to a telesurgical manipulator including: a mounting base; an arm rotatably coupled to the mounting base; a tool actuator assembly coupling movably coupled to the arm such that the tool actuator assembly coupling is translatable relative to the arm, the tool actuator coupling configured to releasably couple with a telesurgical tool actuator assembly; and a link movably coupled between the tool actuator assembly coupling and the arm.

Such a telesurgical manipulator device may optionally include one or more of the following features. The link may be pivotably coupled to the tool actuator assembly and threadably coupled to the arm. The tool actuator assembly coupling may be translatable along an arc defined by the arm. The arm may include a fixed arcuate segment and a movable arcuate segment that is movably coupled with the fixed arcuate segment. The first arcuate segment in combination with the movable arcuate segment may define the pitch arc. The arm may define an elongate opening in which the tool actuator coupling is translatable along a curvilinear path.

In another aspect, this disclosure is directed to a telesurgical system including: a set-up structure releasably coupleable with a frame; a manipulator device; and a telesurgical tool actuator assembly releasably coupleable with the tool actuator assembly coupling. The tool actuator assembly coupling includes a roll-adjustment motor for rotatably driving the surgical tool actuator assembly about the insertion axis. The manipulator device includes: a mounting base releasably coupleable with the set-up structure; an arm rotatably coupled to the mounting base; a tool actuator assembly coupling movably coupled to the arm such that the tool actuator assembly coupling is translatable relative to the arm, the tool actuator assembly coupling defining an insertion axis; and a link movably coupled between the tool actuator assembly coupling and the arm.

Such a telesurgical system may optionally include one or more of the following features. In some embodiments, an entirety of the tool actuator assembly is rotatably drivable by the roll-adjustment motor. A rotatable coupling between the arm and the mounting base defines a yaw axis. The arm defines a pitch arc along which the tool actuator assembly coupling translates. The insertion axis and the yaw axis intersect each other at a center of the pitch arc. The arm may include a fixed arcuate segment and a movable arcuate segment that is movably coupled with the fixed arcuate segment. The first arcuate segment in combination with the movable arcuate segment define the pitch arc.

Some or all of the embodiments described herein may provide one or more of the following advantages. In some cases, the teleoperated manipulator devices provided herein are advantageously structured to have a low profile, i.e., to be spatially-compact. Such a compact configuration is advantageous in that the working space occupied by the teleoperated surgical manipulators above a patient is minimized, allowing for enhanced patient access by surgical personnel. Additionally, greater visualization of the patient and communications between surgical team members is facilitated by the compact manipulator working space.

Further, lessening the size of the manipulator working space can reduce the potential for collisions between manipulators. As a result, the need for redundant degrees of freedom of the manipulators is reduced or eliminated. Hence, the complexity of the manipulators can be lessened in some cases.

The compact size of teleoperated surgical manipulators described herein can also advantageously facilitate mounting the manipulators to a rail of an operating table in some cases. In such a case, as the operating table is manipulated to enhance surgical access, the table-mounted manipulator devices inherently follow. Therefore, the need to reposition the manipulators in response to movements of the operating table is advantageously reduced or eliminated.

In addition, the teleoperated surgical manipulators described herein are advantageously structured to have a relatively low mass and inertia. In addition, the mass distribution is substantially constant such that the inertia is substantially constant, and therefore predictable.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 10 is a perspective view of an example telesurgical system manipulator in accordance with some embodiments.

FIG. 11 is a partially transparent view corresponding to FIG. 10.

FIG. 12 is a side view of the telesurgical system manipulator of FIG. 10.

FIG. 13 is a partially transparent view corresponding to FIG. 12.

FIG. 14 is a top view of the telesurgical system manipulator of FIG. 10.

FIG. 15 is a partially transparent view corresponding to FIG. 14.

FIGS. 18-20 are partially transparent perspective views of the telesurgical system manipulator of FIG. 10 that illustrate pitch motions of the manipulator.

DETAILED DESCRIPTION

Figure 2:
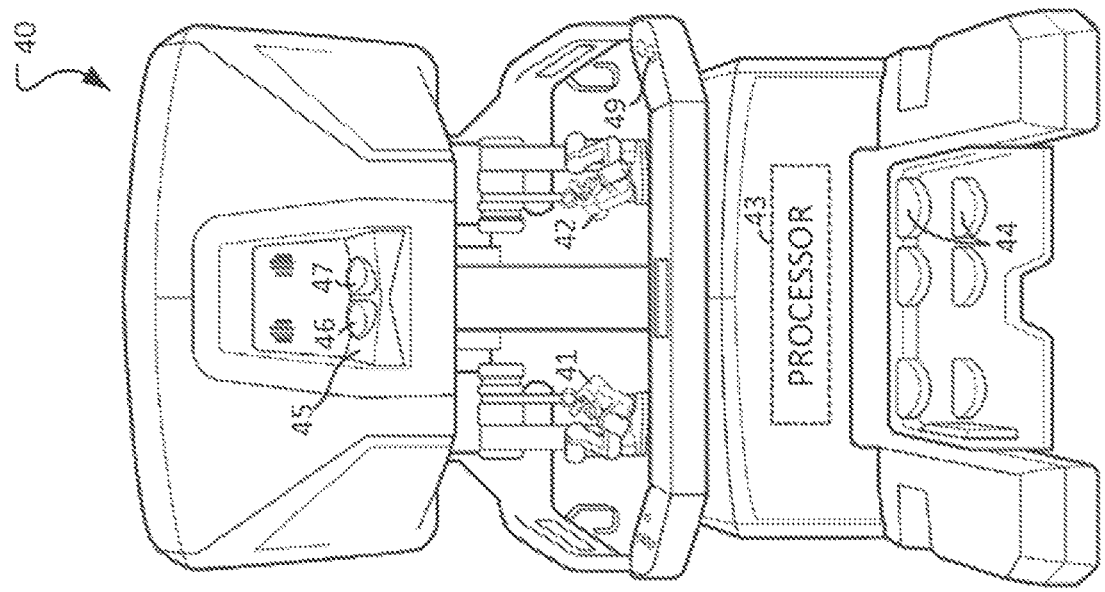
FIG. 2 is a front view of an example user control subsystem of a telesurgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length, and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, the or each of the one or more individual listed items should be considered optional unless otherwise stated, so that various combinations of items are described without an exhaustive list of each possible combination. The auxiliary verb may likewise imply that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae". In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

Inventive aspects are associated with computer-assisted teleoperated surgical systems. An example of a teleoperated surgical system is a da Vinci® Surgical System, commercialized by Intuitive Surgical, Inc. of Sunnyvale, Calif. Knowledgeable persons will understand that inventive aspects disclosed herein may be embodied and implemented in various ways, including completely computer-assisted and hybrid combinations of manual and computer-assisted embodiments and implementations. As applicable, inventive aspects may be embodied and implemented in both relatively smaller, hand-held, hand-operated devices and relatively larger systems that have additional mechanical support, as well as in other embodiments of computer-assisted teleoperated medical devices. In addition, inventive aspects are associated with advances in computer-assisted surgical systems that include autonomous rather than teleoperated actions, and so both teleoperated and autonomous surgical systems are included, even though the description concentrates on teleoperated systems.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller" or "control system", encompasses both centralized single-location and distributed implementations.

This disclosure provides improved surgical and telesurgical devices, systems, and methods. The inventive concepts are particularly advantageous for use with telesurgical systems in which a plurality of surgical tools are mounted on and moved by an associated plurality of teleoperated manipulators during a surgical procedure. The teleoperated surgical systems will often comprise telerobotic, telesurgical, and/or telepresence systems that include one or more processors configured as master-slave controllers. By providing teleoperated surgical systems employing processors appropriately configured to move manipulator assemblies with articulated linkages having relatively large numbers of degrees of freedom, the motion of the linkages can be tailored for work through a minimally invasive access site. The large number of degrees of freedom may also allow a processor to position the manipulators to inhibit interference or collisions between these moving structures, and the like.

The manipulator assemblies described herein will often include a teleoperated manipulator and a tool mounted thereon (the tool often comprising a surgical instrument in surgical versions), although the term "manipulator assembly" will also encompass the manipulator without the tool mounted thereon. The term "tool" encompasses both general or industrial robotic tools and specialized robotic surgical instruments, with surgical instruments often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base that is fixed in space during at least a portion of a telesurgical procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "pose" encompasses both position and orientation. Hence, a change in a pose of an end effector (for example) may involve a translation of the end effector from a first position to a second position, a rotation of the end effector from a first orientation to a second orientation, or a combination of both. As used herein, the term "end effector" therefore includes but is not limited to the function of changing the orientation or position (e.g., a "wrist" function, a parallel motion function) of its distal-most part or parts (e.g., jaw(s) and the like).

When used for minimally invasive teleoperated surgery, movement of the manipulator assembly is controlled by a processor of the system so that a shaft or intermediate portion of the tool is constrained to a safe motion through a minimally invasive surgical access site or other aperture. Such motion may include, for example, axial insertion of the shaft along its long axis through the aperture site, rotation of the shaft about its long axis, and pivotal motion of the shaft about a pivot point (a remote center of motion) on its long axis that is adjacent the access site. But, such motion will often preclude excessive lateral motion of the shaft at the aperture site that might otherwise tear the tissues adjacent the aperture or enlarge the access site inadvertently. Some or all of such constraint on the manipulator motion at the access site may be imposed by using mechanical manipulator joint linkages that inhibit undesired motions (i.e., the hardware constrains motion at the remote center of motion), or the constraint may in part or in full by using robotic data processing and control techniques (i.e., software control constrains motion at the remote center of motion). Hence, such minimally invasive aperture-constrained motion of the manipulator assembly may employ between zero and three degrees of freedom of the manipulator assembly.

Many of the exemplary manipulator assemblies described herein will have more degrees of freedom than are needed to pose and move an end effector within a surgical site in Cartesian space (e.g., 7, 8, 9, 10, or more). For example, a manipulator assembly that can move a surgical end effector in six degrees of freedom in Cartesian space at an internal surgical site through a minimally invasive aperture optionally may have nine degrees of freedom (six end effector degrees of freedom—three for position, and three for orientation—plus three additional manipulator assembly degrees of freedom to comply with access site constraints, collision avoidance, etc.). Highly configurable manipulator assemblies having more degrees of freedom than are needed for a given end effector pose can be described as having or providing sufficient degrees of freedom to allow a range of joint states for an end effector pose in a workspace. For example, for a given end effector position, the manipulator assembly may occupy (and be driven between) any of a range of alternative manipulator linkage poses. Similarly, for a given end effector velocity vector, the manipulator assembly may have a range of differing joint movement speeds for the various joints of the manipulator assembly.

Figure 1:
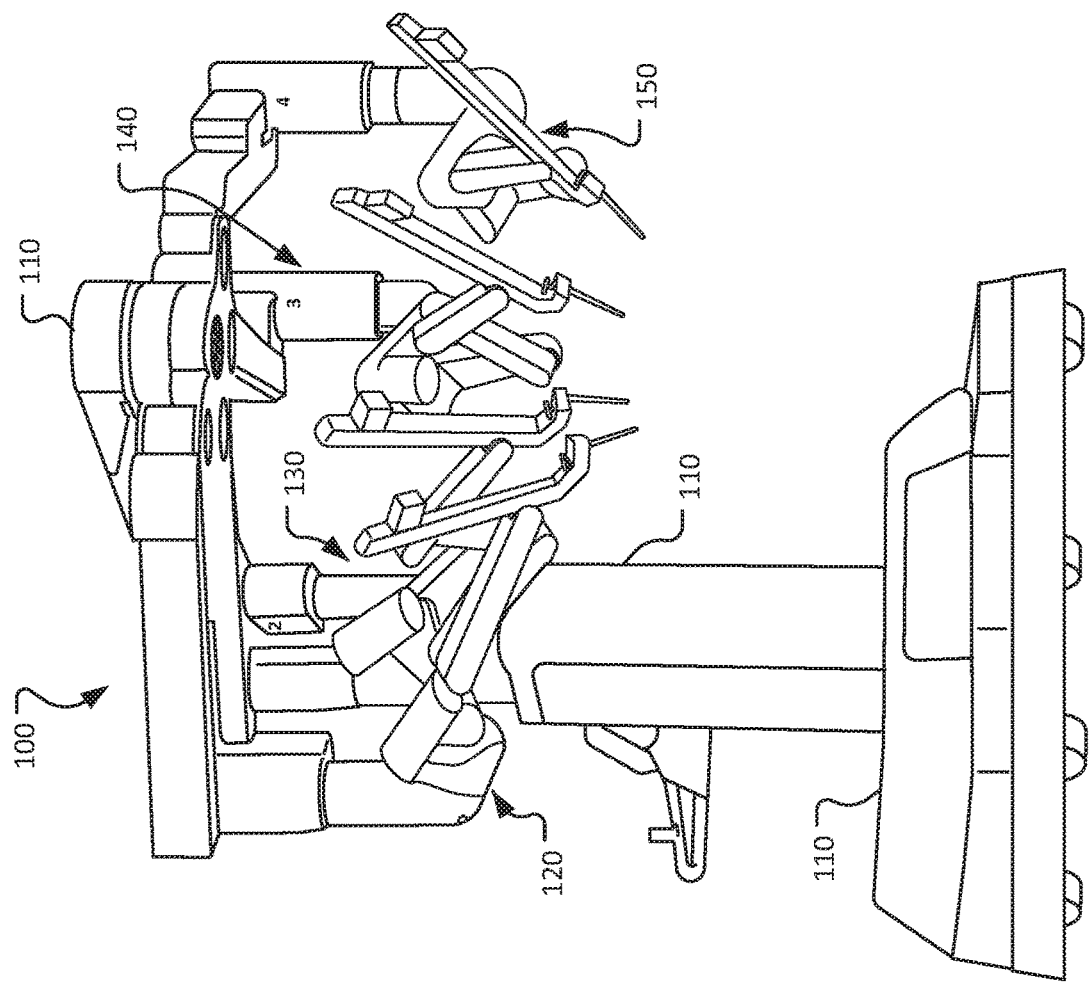
FIG. 1 is a perspective view of an example manipulation subsystem of a telesurgical system.

Referring to FIGS. 1 and 2, telesurgical systems optionally include a manipulating subsystem 100 (e.g., a patient-side unit) and a user control subsystem 40 (e.g., a surgeon control console) at which commands are entered to control tool motion in the manipulating subsystem 100.

In the depicted embodiment, the manipulating subsystem 100 includes a base 110, a first manipulator arm assembly 120, a second manipulator arm assembly 130, a third manipulator arm assembly 140, and a fourth manipulator arm assembly 150. As shown, the base 110 includes a portion that rests on the floor, a vertical column that extends vertically from the base, and a horizontal boom that extends from the top of the column. Other base configurations to mechanically ground the patient-side unit may optionally be used (e.g., ceiling-, wall-, table-mounted, etc.). Each manipulator arm assembly 120, 130, 140, and 150 is pivotably coupled to the base 110. In some embodiments, fewer than four or more than four robotic manipulator arm assemblies may be included as part of the manipulating subsystem 100. While in the depicted embodiment the base 110 includes casters to allow ease of mobility, in some embodiments the manipulating subsystem 100 is fixedly mounted to a floor, ceiling, operating table, structural framework, or the like.

In a typical application, two of the manipulator arm assemblies 120, 130, 140, or 150 each hold a surgical tool, and a third or the manipulator arm assemblies 120, 130, 140, or 150 holds a stereoscopic endoscope. The remaining manipulator arm assembly is available so that another tool may be introduced at the work site. Alternatively, the remaining manipulator arm assembly may be used for introducing a second endoscope or another image capturing device, such as an ultrasound transducer, to the work site.

Each of the manipulator arm assemblies 120, 130, 140, and 150 includes links that are coupled together and manipulated through actuatable (motorized) joints. Each of the manipulator arm assemblies 120, 130, 140, and 150 includes a setup arm portion and a manipulator. The setup arm portion holds the manipulator to place the manipulator's remote center of motion where the tool enters the patient's body at an incision or natural orifice. The device manipulator may then manipulate its tool; so that it may be pivoted about the remote center of motion, inserted into and retracted out of the entry aperture, and rotated about its longitudinal shaft axis.

In the depicted embodiment, the user control subsystem 40 includes a stereo vision display 45 so that the user may view the surgical work site in stereoscopic vision from images captured by the stereoscopic camera of the manipulating subsystem 100. Left and right eyepieces 46 and 47 are provided in the stereo vision display 45 so that the user may view left and right display screens inside the display 45 respectively with the user's left and right eyes. While viewing typically an image of the surgical site on a suitable viewer or display, the surgeon performs a surgical procedure on the patient by controlling one or more master input devices, which in turn control the motion of corresponding tools in the manipulating subsystem.

The user control subsystem 40 also includes left and right master input devices 41, 42 that the user may grasp respectively with the left and right hands to manipulate tools held by the manipulator arm assemblies 120, 130, 140, and 150 of the manipulating subsystem 100 in preferably six or more degrees-of-freedom ("DOF"). Foot pedals 44 are provided on the user control subsystem 40 so the user may control movement and/or actuation of devices associated with the foot pedals. Additional input to the system may be made via one or more other inputs, such as buttons, touch pads, voice, and the like, as illustrated by input 49.

A processor 43 is provided in the user control subsystem 40 for control and other purposes. The processor 43 performs various functions in the telesurgical system. One function performed by processor 43 is to translate and transfer the mechanical motion of master input devices 41, 42 to actuate their respective joints in their corresponding manipulator arm assemblies 120, 130, 140, and 150 so that the user can effectively manipulate tools, such as the surgical tools and endoscopic camera. Another function of the processor 43 is to implement the methods, cross-coupling control logic, and controllers described herein.

Although described as a processor, it is to be appreciated that the processor 43 may be implemented by any combination of hardware, software, and firmware. Also, its functions as described herein may be performed by one unit or divided up among a number of subunits, each of which may be implemented in turn by any combination of hardware, software, and firmware. Further, although being shown as part of or being physically adjacent to the surgeon control unit 40, the processor 43 may also be distributed as subunits throughout the telesurgery system. Accordingly, control aspects referred to herein are implemented via processor 43 in either a centralized or distributed form.

Figure 3:
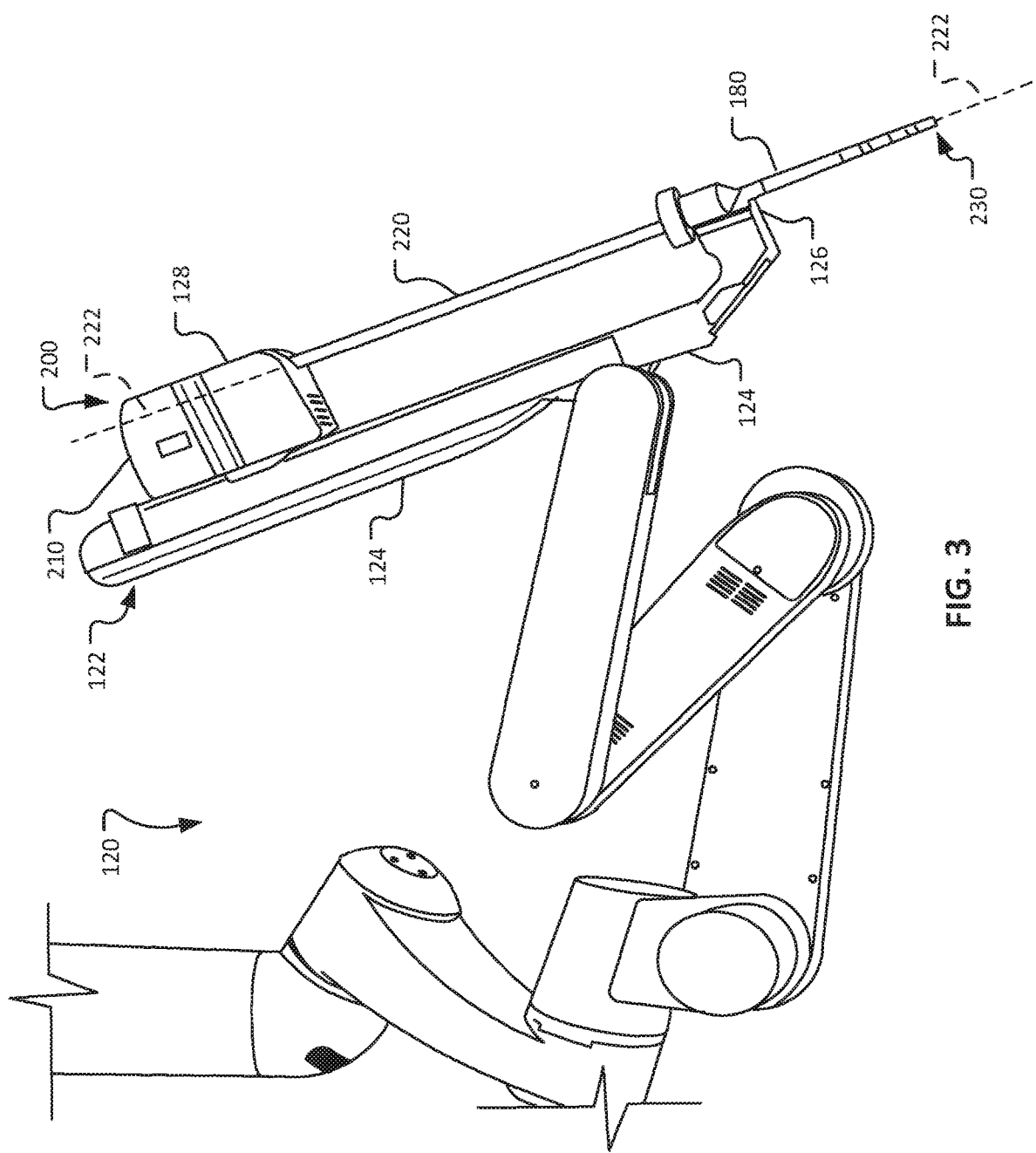
FIG. 3 is a side view of an example telesurgical system manipulator arm assembly.

Referring to FIG. 3, the robotic manipulator arm assemblies 120, 130, 140, and 150 can manipulate tools such as surgical tools to perform minimally invasive surgery. For example, in the depicted arrangement the manipulator arm assembly 120 includes an tool holder assembly 122. A cannula 180 and a surgical tool 200 and are, in turn, releasably coupled to the tool holder assembly 122. The cannula 180 is a tubular member that is located at the patient interface site during a surgery. The cannula 180 defines a lumen in which an elongate shaft 220 of the surgical tool 200 is slidably disposed.

The tool holder assembly 122 includes a spar 124, a cannula clamp 126, and a tool carriage 128. In the depicted embodiment, the cannula clamp 126 is fixed to a distal end of the spar 124. The cannula clamp 126 can be actuated to couple with, or to uncouple from, the cannula 180. The tool holder carriage 128 translates linearly along spar 124 to move a tool coupled to carriage 128 proximally (withdraw) or distally (insert). The movement of the tool holder carriage 128 along spar 124 is controlled by the processor 43, in part while a master control input is controlling insertion and withdrawal movements of the tool. As shown, tool holder carriage 128 includes electric motors that drive mechanical inputs on tool 200 that control end effector and other component movements.

The surgical tool 200 includes a transmission assembly 210, the elongate shaft 220, and an end effector 230. The transmission assembly 210 is releasably coupleable with the tool holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the tool holder carriage 128 translates along the spar 124, the elongate shaft 220 of the surgical tool 200 is moved along the longitudinal axis 222. In such a manner, the end effector 230 can be inserted and/or retracted from a surgical workspace within the body of a patient.

Figure 4:
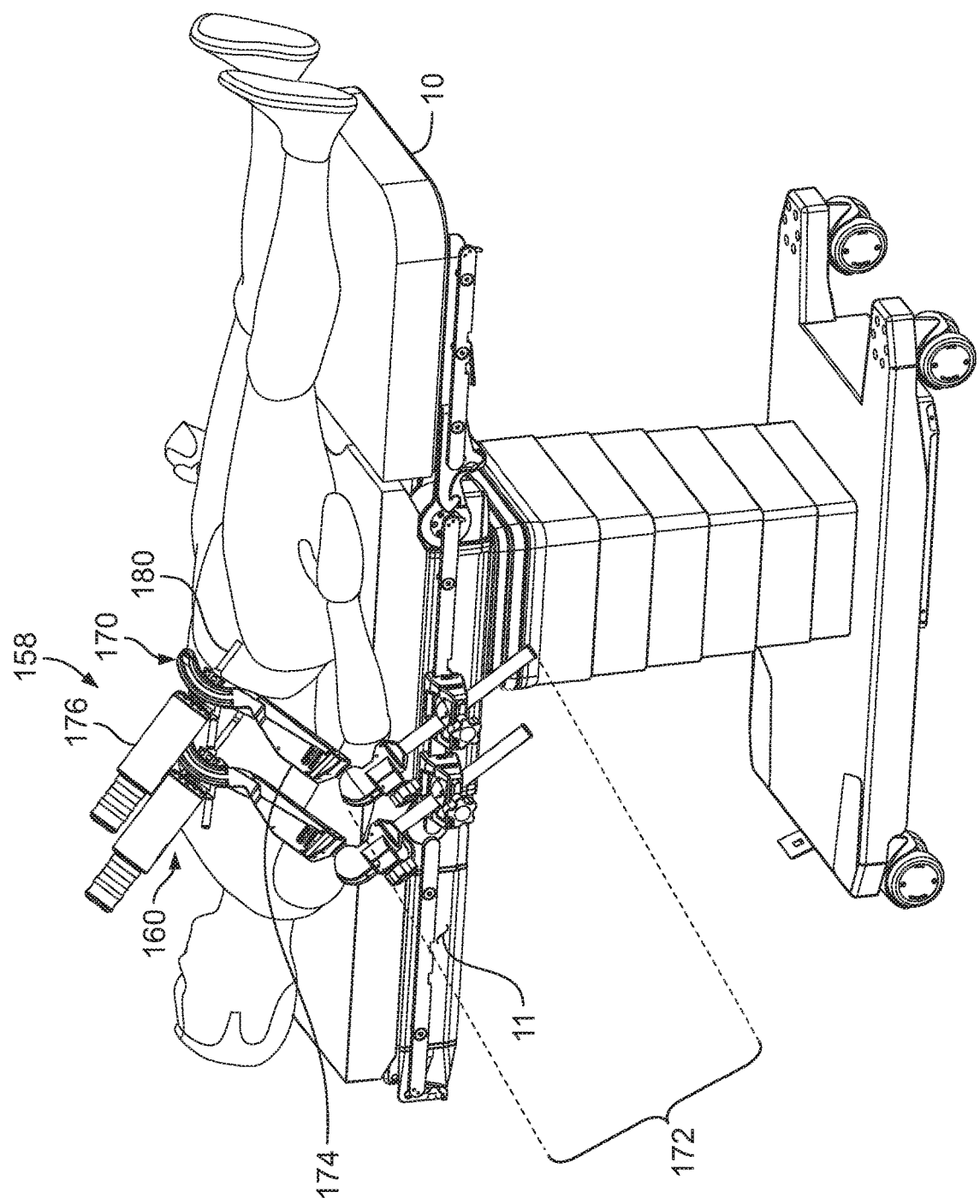
FIG. 4 is a perspective view of another type of manipulation subsystem of a telesurgical system.

Also referring to FIG. 4, another example manipulating subsystem 160 for telesurgery includes a first manipulator arm assembly 162 and a second robotic manipulator arm assembly 164 that are each mounted to an operating table 10. In some cases, this configuration of manipulating system 160 can be used as an alternative to the manipulating subsystem 100 of FIG. 1. While only two manipulator arm assemblies 162 and 164 are depicted, it should be understood that one, or more than two (e.g., three, four, five, six, and more than six) manipulator arm assemblies can be included in some configurations.

In some cases, the operating table 10 may be moved or reconfigured during surgery. For example, in some cases, the operating table 10 may be tilted about various axes, raised, lowered, pivoted, rotated, and the like. In some cases, by manipulating the orientation of the operating table 10, a clinician can utilize the effects of gravity to position internal organs of the patient in positions that facilitate enhanced surgical access (i.e., gravity retraction). In some cases, such movements of the operating table 10 may be integrated as a part of the telesurgical system and controlled by the system.

Figure 5:
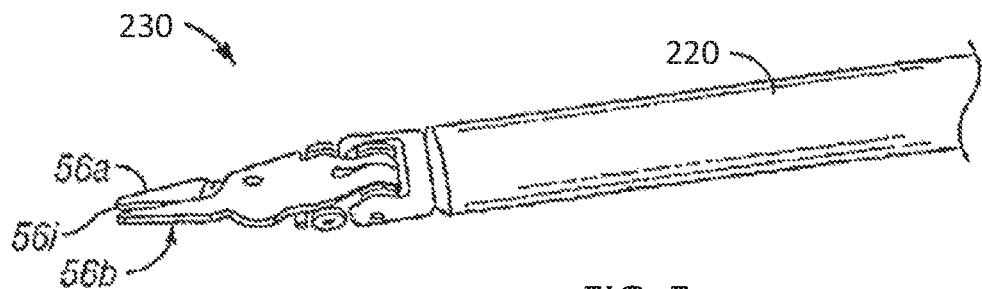
FIG. 5 is a perspective view of a distal end portion of an example surgical tool in a first configuration.
Figure 6:
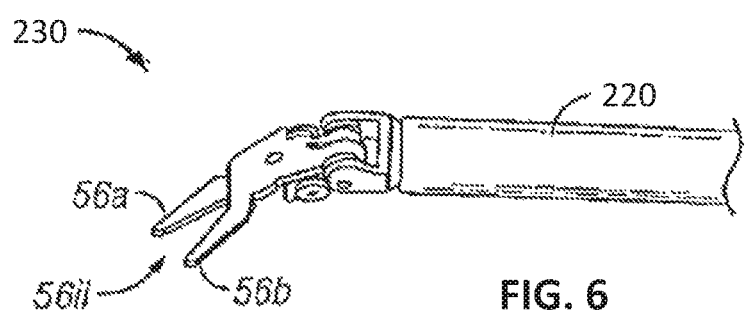
FIG. 6 is a perspective view of the distal end portion of the surgical tool of FIG. 5 in a second configuration.
Figure 7:
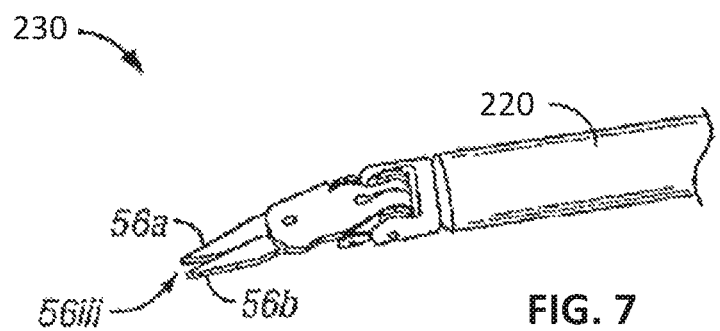
FIG. 7 is a perspective view of the distal end portion of the surgical tool of FIG. 5 in a third configuration.

Also referring to FIGS. 5-7, a variety of alternative telesurgical tools of different types and differing end effectors 230 may be used, with the tools of at least some of the manipulators being removed and replaced with another tool during a surgical procedure. As the manipulator moves, the tool moves as a whole. The manipulator optionally also provides mechanical input to the tool in order to move one or more tool components, such as an end effector. Optionally, a tool may include one or more motors that move an associated one or more tool components. And so, some DOFs are associated with moving the tool as a whole (e.g., tool pitch or yaw about the remote center of motion, tool insertion and withdrawal through the remote center of motion), and some DOFs are associated with moving a tool component (e.g., rolling the end effector by rolling the shaft, end effector pitch or yaw with respect to the shaft, etc.). A tool's end effector is moved by both these types of DOFs, often working in concert to perform the desired end effector pose change in space. It can be seen that the manipulator arm assemblies 120, 130, 140, and 150 will often undergo significant movement outside patient during a surgical procedure in order to move a corresponding tool end effector as commanded by the corresponding master input device.

End effectors may include first and second end effector elements 56a, 56b which pivot relative to each other so as to define a pair of end effector jaws, for example DeBakey Forceps 56i, microforceps 56ii, and Potts scissors 56iii. Other end effectors may have a single end effector element, for example scalpels and electrocautery elements. For tools having end effector jaws, the jaws will often be actuated by squeezing grip members on master input devices 41, 42. Other end effector mechanical DOFs may include functions such as staple application, clip application, knife blade movement, and the like.

Figure 8:
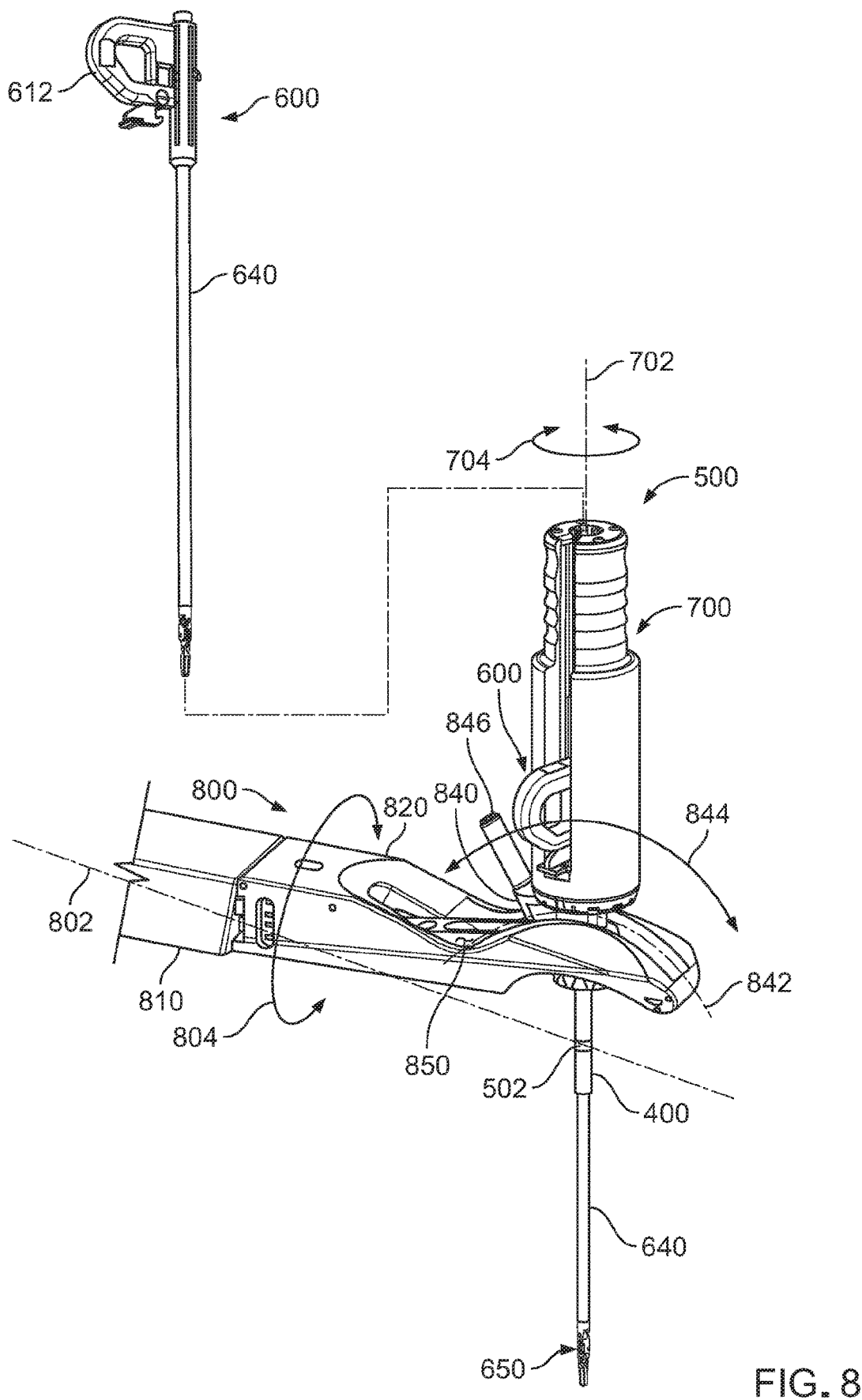
FIG. 8 is a perspective view depicting a surgical tool coupled with a surgical tool actuation assembly pod that is mounted to an example telesurgical manipulator assembly in accordance with some embodiments.

Referring to FIG. 8, an example telesurgical system 500 includes a surgical tool 600, a surgical tool actuator assembly 700 (also referred to herein as a "pod"), and a manipulator assembly 800. Pod 700 is compatible with tool 600, and tool 600 is removably coupled to Pod 700. Pod 700 is coupled to manipulator assembly 800. In some embodiments, the pod 700 is readily detachable from the manipulator assembly 800 such that the pod 700 can be conveniently interchanged with another pod. The manipulator assembly 800 can be adjustably mounted to a frame or a structure (such as the set-up structure 172 of FIG. 4). Manipulator assembly 800 and pod 700 together form a manipulator.

When surgical tool 600 is coupled with pod 700, a shaft 640 of the surgical tool 600 slidably extends through a cannula 400 that is releasably coupled to the manipulator assembly 800. In use, the cannula 400 can extend through a patient's body wall or natural orifice. Surgical tool 600 includes an end effector 650 that is controlled by the user operating a master input device to perform telesurgery.

Pod 700 defines a space configured to receive surgical tool 600. When the surgical tool 600 is coupled pod 700, pod 700 can actuate movements of the surgical tool 600 as a whole and movements of the end effector 650 with reference to the main body of the tool. For example, the pod 700 can actuate translational movements of the surgical tool along the longitudinal axis 702 of the pod 700 to insert or withdraw the end effector. Hence, the longitudinal axis 702 may also be referred to as the insertion axis 702, which is coincident with tool 600's long axis.

The manipulator assembly 800 includes a mounting base 810, an arm 820, a tool actuator assembly coupling 840 (a "pod coupling"), and a drive link 850. The mounting base 810 is configured to releasably couple with a set-up structure of a telesurgical system (such as the set-up structure 172 of FIG. 4). The arm 820 is rotatably coupled to the mounting base 810 to rotate about axis 802.

Pod coupling 840 is configured to releasably couple with pod 700, and it is movably coupled with the arm 820 such that pod coupling 840 is translatable along an arcuate path defined by the arm 820 (a "pitch arc"). As shown, the pitch arc 842 is defined in a distal portion of arm 820.

The drive link 850 is movably coupled between the arm 820 and the pod coupling 840. A first end of the link 850 is coupled to an actuator of the arm 820. A second end of the link 850 is coupled to the pod coupling 840. Hence, an actuator in arm 820 drives pod coupling 840 along the pitch arc 842 via drive link 850.

The telesurgical system 500 is configured to actuate pitch, roll, and yaw motions of the surgical tool 600 in response to input (e.g., user input using the control subsystem 40 as described in reference to FIG. 2). For example, the arm 820 is rotatably coupled to the mounting base 810 such that the arm 820 can be controlled to rotate about yaw axis 802 in relation to mounting base 810, as indicated by arrows 804. In addition, the tool actuator assembly coupling 840 is movably coupled to the arm 820 such that the tool actuator assembly coupling 840 can be controlled to translate along pitch arc 842 as indicated by arrows 844. Further, at pod coupling 840, pod 700 is rotatable about insertion axis 702 in relation to the arm 820, as indicated by arrows 704. As shown, in some embodiments pod coupling 840 includes a motor 846 that drives pod 700 rotation about axis 702.

In some embodiments (such as the depicted embodiment), the insertion axis 702 and the yaw axis 802 intersect each other at a center point of the pitch arc 842 to define a remote center of motion 502. The remote center of motion 502 is a point in space around which the roll, pitch, and yaw motions described above are made. For example, as the arm 820 is rotated in relation to the mounting base 810 to generate a yaw motion of the surgical tool 600, the position of the remote center of motion 502 is unchanged because the yaw axis 802 passes through the remote center of motion 502. In addition, as the pod coupling 840 is translated in relation to the arm 820 along the pitch arc 842 to generate a pitch motion of the surgical tool 600, the position of the remote center of motion 502 is unchanged because the center point of the pitch arc 842 is located at the remote center of motion 502. Further, as the pod 700 is rotated in relation to the arm 820 about the insertion axis 702 to generate a roll motion of the surgical tool 600, the position of the remote center of motion 502 is unchanged because the insertion axis 702 passes through the remote center of motion 502. Hence, it can be said that telesurgical system 500 is a hardware-constrained remote center of motion system.

In use, the remote center of motion 502 (which is typically at a location coincident with a region of the cannula 400) may be positioned at the patient's body wall or natural orifice. One advantage of such an arrangement is that while the surgical tool 600 undergoes roll, pitch, and yaw motions, the resulting trauma applied to the body wall by the cannula 400 is reduced or eliminated because the portion of the cannula 400 (at the remote center of motion 502) that interfaces with the body wall moves a relatively small amount while the surgical tool 600 undergoes the roll, pitch, and yaw motions.

Further, in regard to the hardware-constrained remote center of motion, it should be understood that at all pod 840 positions along pitch arc 842, the insertion axis 702 and the yaw axis 802 intersect each other at the center of the pitch arc where the remote center of motion 502 is located. In addition, at all positions about the yaw axis 802 of the arm 820 relative to the mounting base 810, the insertion axis 702 and the yaw axis 802 intersect each other at the center of the pitch arc where the remote center of motion 502 is located. Further, at all positions of the pod coupling 840 along the pitch arc 802 in combination with any position about the yaw axis 802 of the arm 820 relative to the mounting base 810, the insertion axis 702 and the yaw axis 802 intersect each other at a center of the pitch arc where the remote center of motion 502 is located.

Figure 9:
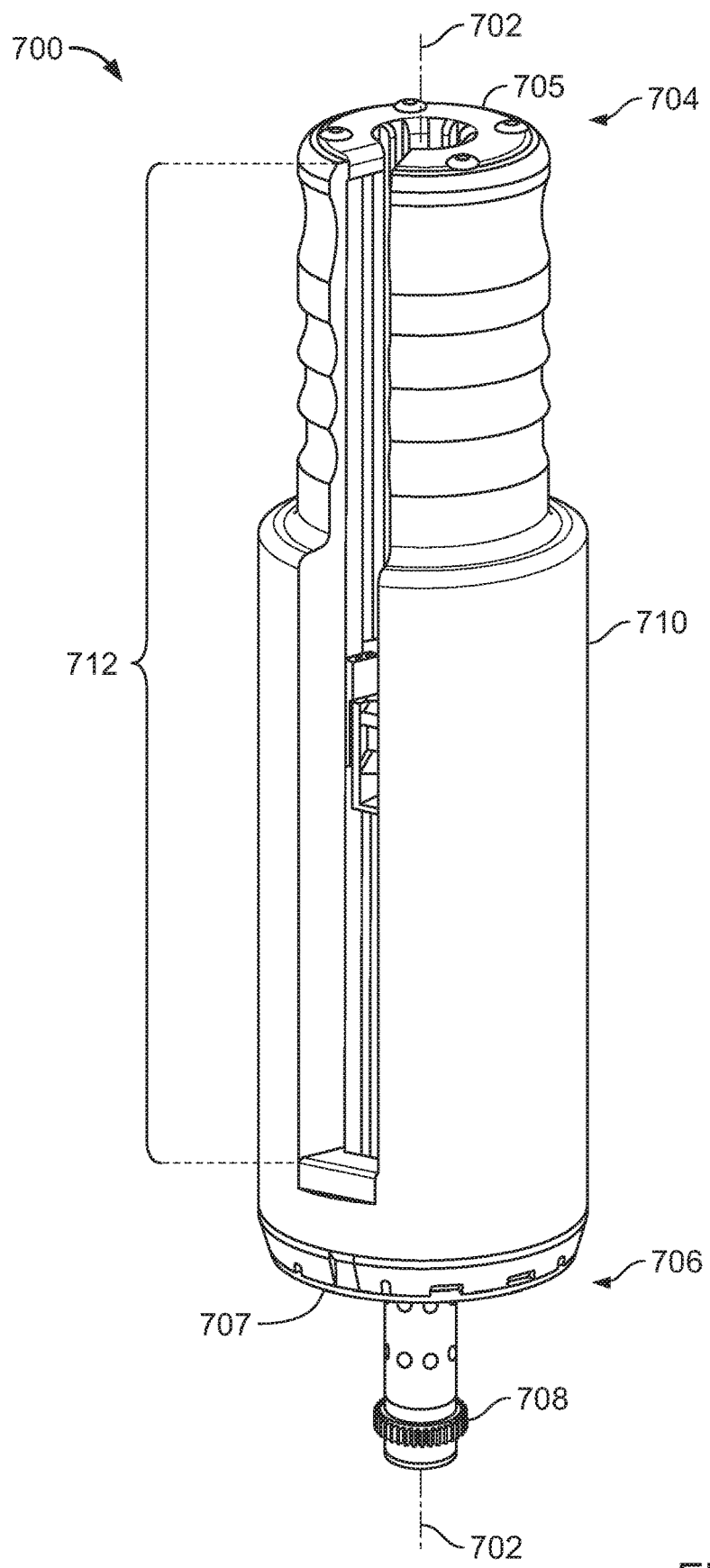
FIG. 9 is a perspective view of an example surgical tool actuation assembly pod in accordance with some embodiments.

Referring also to FIG. 9, pod 700 is shown in isolation from the surgical tool 600 and the manipulator assembly 800. Pod 700 includes a proximal end 704 and a distal end 706, and the longitudinal axis 702 is defined between these proximal and distal ends.

In the depicted embodiment, the pod 700 includes a proximal end plate 705, a distal end plate 707, and a housing 710. The housing 710 extends between the proximal end 704 and the distal end 706.

In the depicted embodiment, the proximal end plate 705 is a C-shaped plate, and the distal end plate 707 is a fully circumferential plate that defines an open center. The opening in the proximal end plate 705 aligns with a slot opening 712 defined by the housing 710. The slot opening 712 and the opening in the C-shaped proximal end plate 705 provide clearance for a handle 612 of the surgical tool 600 to project radially from the housing 710 while the surgical tool 600 is coupled with the tool drive system 700.

In the depicted embodiment, pod 700 also includes a roll driven gear 708 located at the distal end 706. The pod's roll driven gear 708 can mesh with and be driven by a roll drive gear 847 (refer to FIGS. 13, 17, and 19) coupled to a roll drive motor 846 of the pod coupling 840 when the pod 700 is coupled with the manipulator assembly 800. When the roll drive gear 847 drives the roll driven gear 708, the entire pod 700 rotates to roll about the longitudinal axis 702. As a result, when the surgical tool 600 is engaged with the pod 700, the surgical tool 600 as a whole also rotates to rolls about the longitudinal axis 702 (i.e., about shaft 640). Alternatively, in some embodiments, a roll drive motor (to which a roll drive gear is coupled) is a component of the pod 700, and a roll driven gear is a component of the pod coupling 840. The roll driven gear can be fixed to the pod coupling 840 in some embodiments. In such an arrangement, when the roll driven gear is driven by the roll drive motor, the entire pod 700 rotates to rolls about the longitudinal axis 702. Rotating the tool as a whole rotates the tool's end effector, and so the tool may be simplified by eliminating an end effector DOF for roll with reference to the main body of the tool.

Referring also to FIGS. 10, 12, and 14, the example manipulator assembly 800 is shown in isolation from the surgical tool 600 and the pod 700. In the example embodiment, it can be seen that the proximal end of mounting base 810 includes a ball configured to releasably couple with a corresponding socket in a set-up structure of a telesurgical system (such as the set-up structure 172 of FIG. 4). The ball and socket form a spherical joint that advantageously allows the mounting base to be posed in various ways to align with a cannula for surgery. In other embodiments, other joint configurations may be used between the manipulator and the setup portion of the arm.

In the depicted embodiment, the pod coupling 840 includes roll drive motor 846 that drives pod 700 to rotate about insertion axis 702. An open interior space is defined in pod coupling 840. This open space receives pod 700's distal end portion 706 and is aligned with insertion axis 702 when pod 700 is mounted on pod coupling 702. Inserting pod 700's distal end portion 706 engages the pod with roll drive motor 846, which may then drive pod 700 to roll about insertion axis 702. Details of roll drive motor 846 placement are discussed further below.

The link 850 is movably coupled between the arm 820 and the pod coupling 840. A first end of the link 850 is coupled to an actuator (e.g., a linear actuator) of the arm 820. A second end of the link 850 is coupled to the pod coupling 840. Hence, the pod coupling 840 is driven along the curvilinear path of the pitch arc 842 by the link 850 that is driven by an actuator of the arm 820. Various linear actuator types may be used, including motors that drive lead or ball screws with threaded nuts that translate as the screw turns, chain or belt drives, hydraulic or pneumatic actuators, electromagnetic or piezo electric linear drives, and the like.

Referring also to FIGS. 11, 13, and 15, portions of the example manipulator assembly 800 are shown transparently so internal components of the manipulator assembly 800 can be visualized.

First, the mechanisms used for yaw motions of the manipulator assembly 800 will be described. The arm 820 includes a cylindrical projection 822 that extends into an internal space defined by the mounting base 810 and forms a roll joint between the arm and the mounting base. Spaced-apart yaw bearings 824*a* and 824*b* are disposed between the projection 822 and the internal space defined by the mounting base 810 to provide for the rotatable interface between base 810 and arm 820. The longitudinal axis of the cylindrical projection 822 defines the yaw axis 802. A yaw-adjustment motor 826 is disposed within the arm 820, with an axis of rotation parallel to and offset from yaw axis 802. A yaw drive gear 828 is driven by the yaw-adjustment motor 826. The yaw drive gear 828 is meshed with a yaw driven gear 806 that is affixed in a stationary relationship to the mounting base 810 and around yaw axis 802. In the depicted embodiment, the yaw driven gear 806 is a sector gear (e.g., an arcuate gear rack) sufficient to accommodate the desired yaw range of motion. While the mounting base 810 is held stationary by a set-up structure, actuation of the yaw-adjustment motor 826 will rotate the yaw drive gear 828, which will then travel along a circular path around the yaw driven gear 806 (i.e., around yaw axis 802). As a result, the arm 820 will rotate about the yaw axis 802 in relation to the mounting base 810. Optionally, however, a projection may extend from base 810 into arm 820, and the components described above modified accordingly. And, optionally the motor and drive gear may be stationary in base 810 and drive arm 820 to rotate.

Now the mechanisms used for pitch motions of the manipulator assembly 800 will be described. The arm 820 includes a pitch-adjustment motor 830. In the depicted embodiment, two pitch-adjustment motors 830 are ganged together for greater torque, but two motors are not required in all embodiments. In some embodiments, a single pitch-adjustment motor 830 is included. A pitch drive gear 832 coupled to the shaft of the pitch-adjustment motor 830 is rotated by the pitch-adjustment motor 830. A pitch driven gear 834 is driven by the pitch drive gear 832. In some embodiments, one or more intermediate gears may be positioned between the pitch drive gear 832 and the pitch driven gear 834. The pitch driven gear 834 is affixed to a lead screw 836 that is rotatably coupled within the arm 820. Thus, the lead screw 836 is rotated about its longitudinal axis as the pitch driven gear 834 is rotated by the pitch drive gear 832 (which is rotated by the pitch-adjustment motor 830). A nut 838 is threadably coupled with the lead screw 836. The nut 838 is restrained from rotating along with the lead screw 836 as the lead screw 836 is rotating. Therefore, as the lead screw 836 rotates, the nut 838 translates along the longitudinal axis of the lead screw 836. A first end 852 of the link 850 is pivotably coupled to the nut 838. A second end 854 of the link 850 is pivotably coupled to the pod coupling 840. Hence, as the nut 838 translates along the longitudinal axis of the lead screw 836, the second end 854 of the link 850 drives translation of the pod coupling 840. Translations of the pod coupling 840 follow the curvilinear path of the pitch arc 842. That is the case because the pod coupling 840 includes four bearings 848 that travel within arcuate grooves 821 defined within the arm 820. The arcuate grooves 821 define the pitch arc 842. Other embodiments optionally use other pitch arc designs, such as a single arcuate groove with one or more bearings, one or more arcuate rails with bearings on either side, one or more parallel arcuate rails with individual bearings inside each rail, one or more arcuate gear racks with mating pinions, one or more arcuate rods with one or more bearings sliding on the rod, and the like. And, other linear actuator types may be used, as described above.

Figure 16:
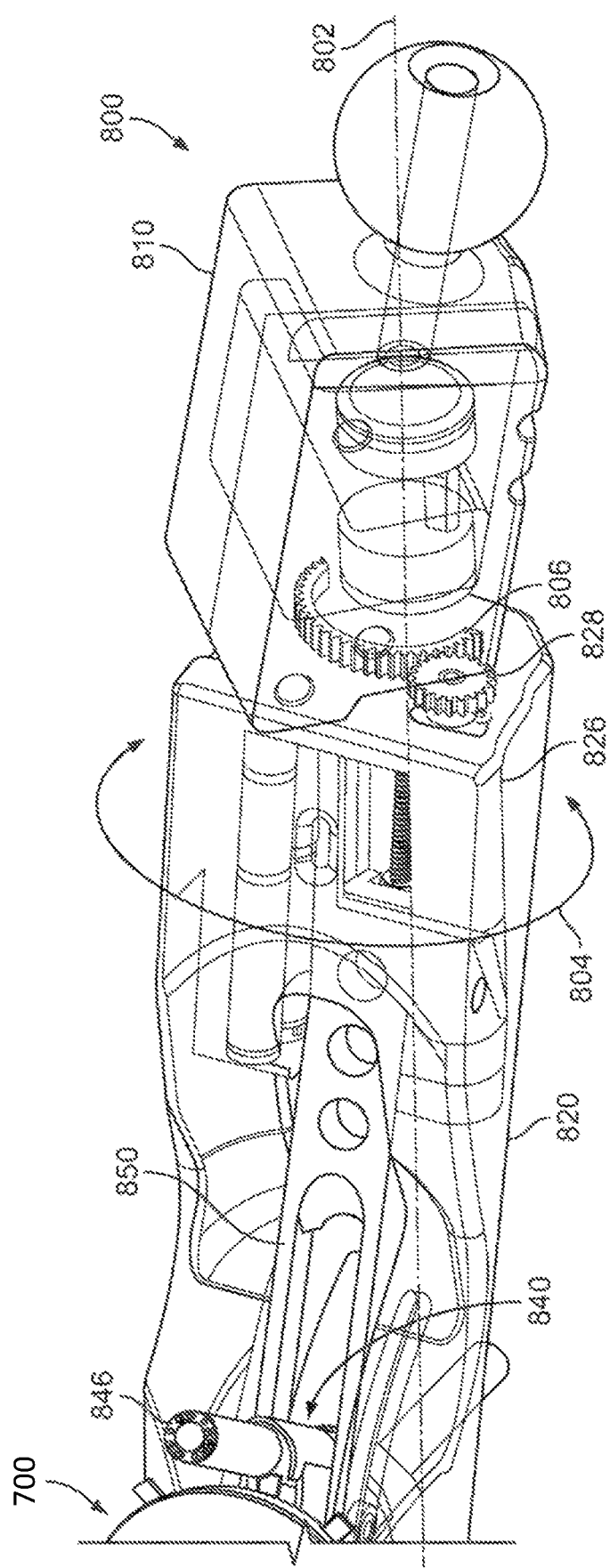
FIGS. 16 and 17 are partially transparent perspective views of the telesurgical system manipulator of FIG. 10 that illustrate yaw motions of the manipulator.
Figure 17:
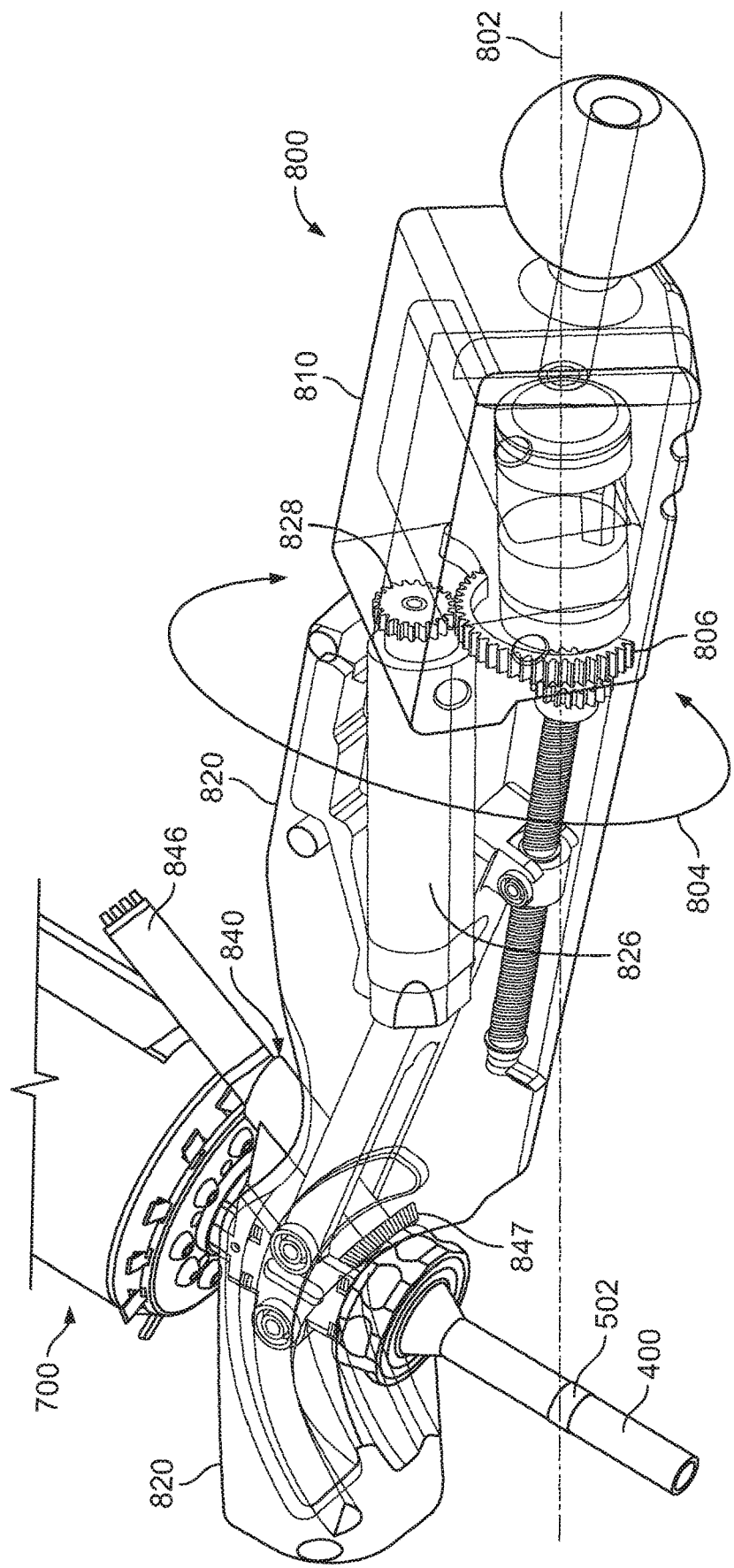

Referring to FIGS. 16 and 17, yaw motions (as represented by arrow 804) of the example manipulator device 800 can be further visualized. The mounting base 810 is stationary (e.g., coupled to a set-up structure), and the arm 820 is rotatable about the yaw axis 802 in relation to the mounding base 810.

The arm 820 includes the yaw-adjustment motor 826. The yaw drive gear 828 is rigidly coupled to the shaft of the yaw-adjustment motor 826. Hence, actuation of the yaw-adjustment motor 826 will rotate the yaw drive gear 828. The yaw-adjustment motor 826 can rotate bi-directionally.

The yaw drive gear 828 is meshed with the yaw driven gear 806 that is affixed in a stationary relationship to the mounting base 810 and around the yaw axis 802. Since the mounting base 810 is held stationary by a set-up structure, actuation of the yaw-adjustment motor 826 (which rotates the yaw drive gear 828) will cause the yaw drive gear 828 to travel along a circular path around the yaw driven gear 806. In result, the arm 820 will rotate in relation to the mounting base 810 about the yaw axis 802.

In the depicted embodiment, the manipulator device 800 can rotatably adjust through a range of about 160° of yaw motion. That is, the arm 820 can rotate in relation to the mounting base 810 about the yaw axis 802 through about 160° of travel. In some embodiments, the manipulator device 800 is configured to facilitate a range of yaw motion of about 90° to about 130°, about 100° to about 140°, about 110° to about 150°, about 120° to about 160°, about 130° to about 170°, or about 140° to about 180°. Yaw range of motion may be constrained by hardware (e.g., the end of an arcuate rack, a physical hard stop between base and arm, and the like) or may be constrained by software control of motor 826.

Placing the manipulator assembly yaw and pitch actuator motors in arm 820 advantageously allows base 810 to be relatively short, allows the pitch drive to be folded back on itself, and allows the yaw drive to occupy the same length as the pitch drive for an overall compact arm and manipulator assembly design.

Figure 20:
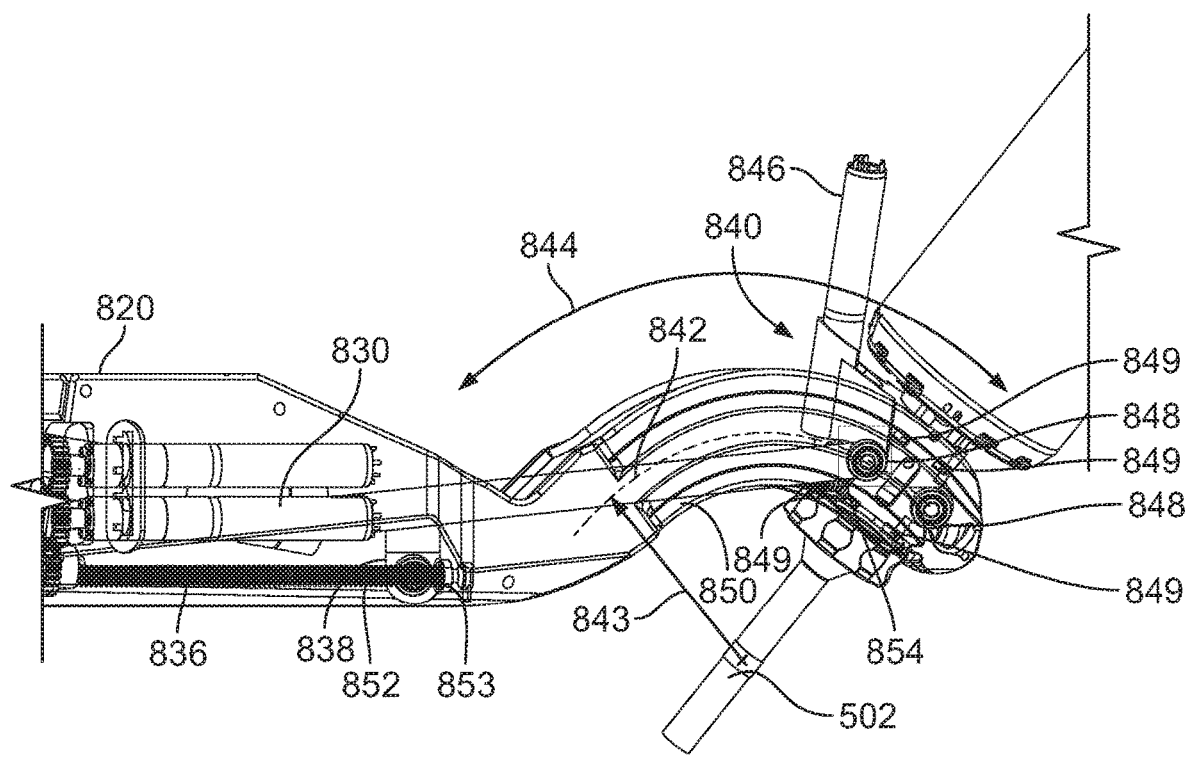

Referring to FIGS. 18-20, pitch motions (as represented by arrow 844) of the example manipulator assembly 800 can be further visualized. The pitch motions of the manipulator assembly 800 entail curvilinear translational movements of the pod coupling 840 along the pitch arc 842 as indicated by arrow 844.

The arm includes one or more pitch-adjustment motors 830 which bi-directionally, rotatably drive the leadscrew 836. The nut 838 is threadably coupled to the leadscrew 836 and is rotationally constrained such that rotations of the leadscrew 836 result in translational movements of the nut 838. The first end 852 of the link 850 is pivotably coupled to the nut 838. The second end 854 of the link 850 is pivotably coupled to the pod coupling 840. Hence, as the nut 838 translates along the longitudinal axis of the lead screw 836, the second end 854 of the link 850 drives translation of the pod coupling 840. Translations of the pod coupling 840 follow the curvilinear path of the pitch arc 842 because the pod coupling 840 includes four bearings 848 that travel within the arcuate grooves 821 (FIGS. 11 and 13) defined within the arm 820. The arcuate grooves 821 define the pitch arc 842. The four bearings 848 are advantageously spaced apart from each other so as to provide structural stability and rigidity of the pod coupling 840 in relation to the arm 820.

Forces from the surgical tool 600 and/or cannula 400 (FIG. 8) that are generally parallel with the insertion axis 702 are transferred to the arm 820 via the four spaced-apart bearings 848 that travel within arcuate grooves 821 defined within the arm 820. Forces from the surgical tool 600 and/or cannula 400 that are transverse to the insertion axis 702, and torsional forces from the surgical tool 600 and/or cannula 400, are transferred to the arm 820 via multiple bearings 849. The bearings 849 are rotatably coupled to the pod coupling 840 and roll on inner planar surfaces of the arm 820. In the depicted embodiment, eight bearings 849 are included (four on each side of the pod coupling 840 that rides within the distal arcuate portion of the arm 820). These eight bearings 849 are spaced apart from each other to advantageously provide structural stability and rigidity of the pod coupling 840 in relation to the arm 820. In some embodiments, more or fewer than eight bearings 849 are included. For example, in some embodiments two, three, four, five, six, seven, nine, ten, eleven, twelve, or more than twelve bearings 849 are included.

The center point of the radius 843 of the pitch arc 842 is coincident with the remote center of motion 502. Hence, pitch motions of the manipulator device 800 are made about the remote center of motion 502 because the center point of the radius 843 of the pitch arc 842 is coincident with the remote center of motion 502.

In the depicted embodiment, the manipulator device 800 can adjust through a range of about 80° of pitch motion. That is, the pod coupling 840 can translate in relation to the arm 820 along the pitch arc 842 through about 80° of travel. In some embodiments, the manipulator device 800 is configured to facilitate a range of pitch motion of about 50° to about 70°, about 60° to about 80°, about 70° to about 90°, about 80° to about 100°, about 90° to about 110°, or about 100° to about 120°. Range of motion may be constrained by physical hard stop, such as reaching the end of an arcuate groove or a dedicated mechanical stop, or it may be constrained by software control of the motor.

The range of pitch motion of the manipulator device 800 is advantageously facilitated in part by the configuration of the link 850. That is, the second end 854 of the link 850 is forked to provide clearance for the roll-adjustment motor 846 to travel within the space between the forks while the pod coupling 840 is positioned in relation to the arm 820 as shown in FIGS. 10-11, 14-16, and 18-20. Placing the roll drive motor 846 proximally on the pod coupling 820 prevents the motor from projecting distally and interfering with another manipulator or surgical tool or clinical personnel as the surgical tool is driven to its full pitch-back range of motion limit, and forking the link 850 allows the motor to travel within the link to increase the surgical tool's full pitch-forward range of motion limit. Alternatively, however, the roll drive motor may be placed distally or to the side on the pod coupling. And, rather than forking link 850, a non-forked single link offset to the side of motor 846, or two links on either side of link 846, may optionally be used.

As described previously, the nut 838 is constrained from rotating. One mechanism by which the nut 838 is so constrained also advantageously helps prevent or reduce the exertion of undesirable lateral forces to the leadscrew 836. In particular, the arm 820 defines two elongate linear channels 839 (e.g., refer to FIG. 13) that extend parallel to the leadscrew 836 on opposite sides of the leadscrew 836. Two bearings 853 are movably engaged within the two elongate linear channels 839. The two bearings 853 can be rotatably coupled with the nut 838 or with the first end 852 of the link 850. This arrangement will transfer forces from the link 850 (that would otherwise be exerted laterally to the leadscrew 836) via the bearings 853 to the elongate linear channels 839.

In some embodiments, the manipulator assembly 800 may include electronic sensors and the like for various advantageous purposes. For example, encoders may be coupled to the drive trains of the motorized pitch, roll, and/or yaw adjustment mechanisms. In some embodiments, position sensors may be used that can positively identify the locations of the movable components of the manipulator device 800.

Figure 21:
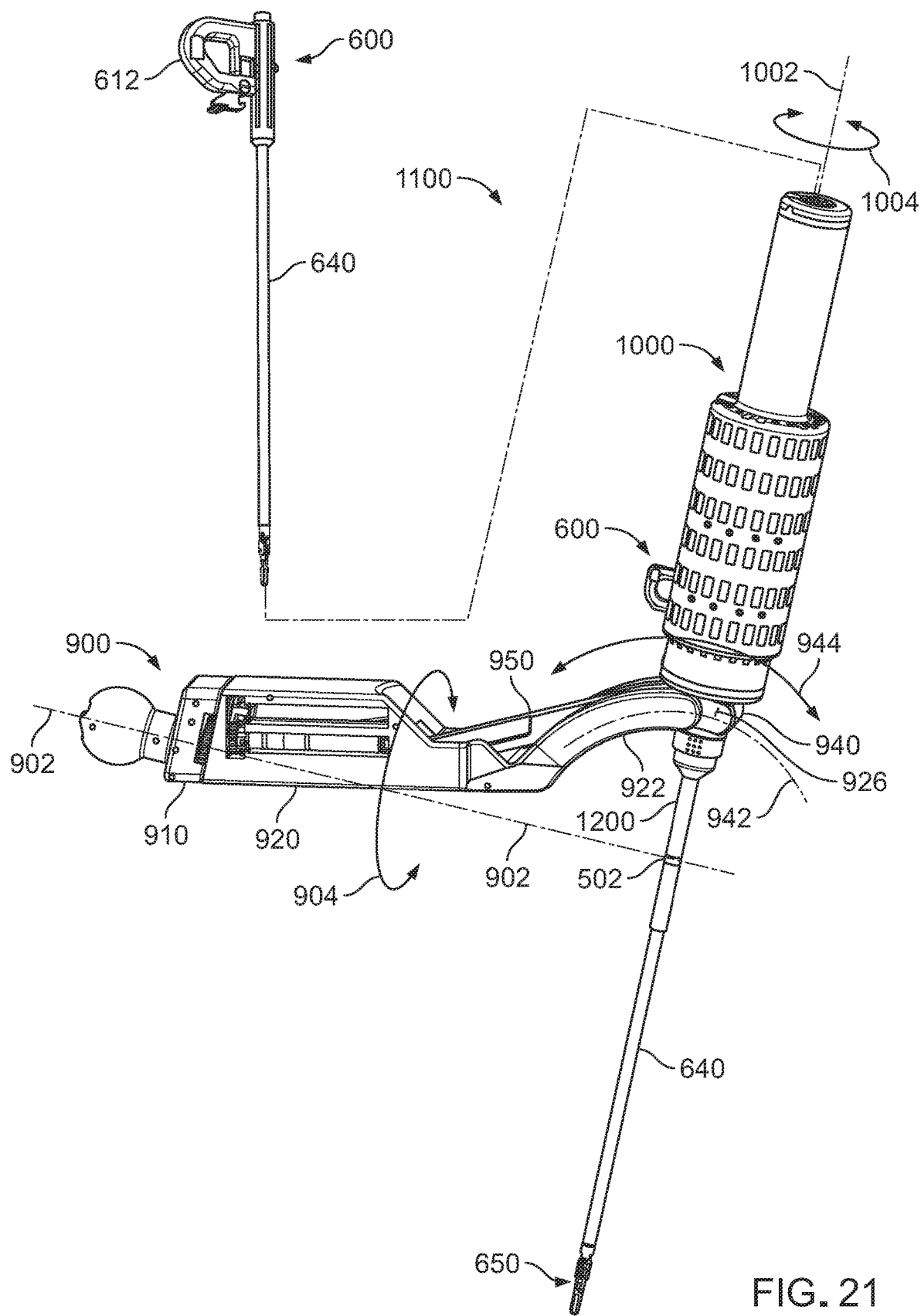
FIG. 21 is a perspective view depicting a surgical tool coupled with a surgical tool actuation assembly pod that is mounted to another example telesurgical system manipulator in accordance with some embodiments.

Referring to FIG. 21, another example telesurgical system manipulator 1100 includes the surgical tool 600 that is selectively coupleable with a compatible surgical tool actuator assembly 1000 (again, a "pod") that is, in turn, coupleable with an example manipulator assembly 900 to form a teleoperated tool manipulator. The configuration of surgical tool 600 is as described above, and the description of pod 700 above generally applies to pod 1000, with certain differences noted in the description below. Manipulator assembly 900 and its components are generally similar to manipulator assembly 800 and its components (e.g., base, arm, pod coupling) as described above, with certain differences noted in the description below. Cannula 1200 and its mounting is generally similar to cannula 400 described above. The remote center of motion 502 and associated yaw, pitch, and insertion axes are as described above.

As shown in FIG. 21, the surgical tool actuator assembly coupling 940 (again, a "pod coupling") is movably coupled with the arm 920 such that pod coupling 940 translates along an arcuate path 942 (again, the "pitch arc") defined by the distal portion of arm 920. In the depicted embodiment the arcuate path 942 is defined by a combination of a fixed arcuate segment 922 (i.e., fixed in relation to other main portions of the arm 920) and a movable arcuate segment 926. The movable arcuate segment 926 is movably coupled to the fixed arcuate segment 922 in a telescopic arrangement, as described further below in reference to FIGS. 22-24.

The link 950 is similar to link 850 and is movably coupled between the arm 920 and the pod coupling 940. A first end of the link 950 is coupled to an actuator of the arm 920 that is similar to the pitch-adjustment actuator of arm 820. A second end of the link 950 is coupled to pod coupling 940. Hence, pod 940 is driven along the curvilinear path of the pitch arc 942 by the link 950 that is driven by an actuator of the arm 920.

The telesurgery surgery system 1100 is configured to actuate yaw, pitch, and roll motions of surgical tool 600 in response to user input as described above, with arm 820 rotating around associated yaw axis 902 (arrows 904), pod coupling 940 translating along pitch arc 942 (arrows 944), and pod 1000 rotating around insertion axis 1002 (arrows 1004). As described above, pod 1000 controls tool insertion and withdrawal along axis 1002 and tool 600 distal component movements.

Figure 22:
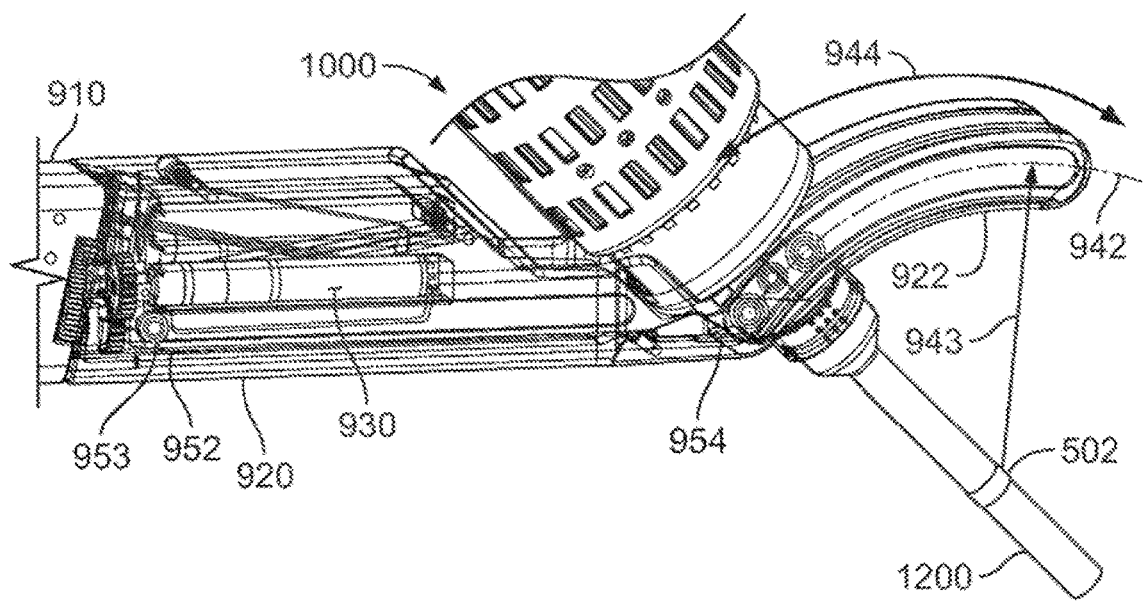
FIGS. 22-24 are partially transparent perspective views of the telesurgical system manipulator of FIG. 21 that illustrate pitch motions of the manipulator.
Figure 23:
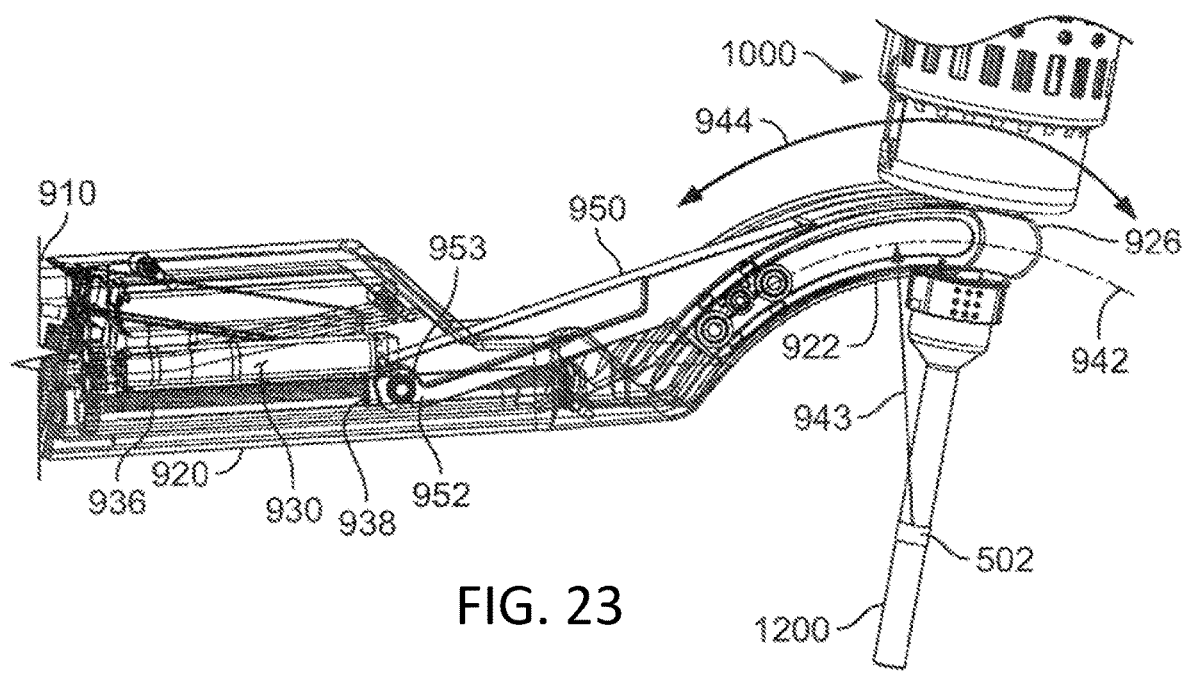
Figure 24:
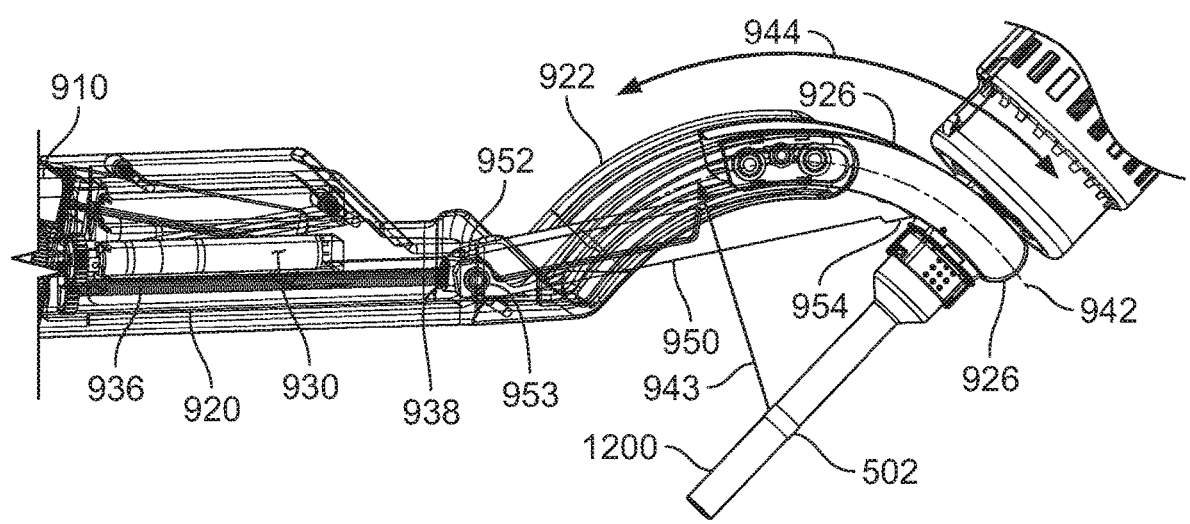

Referring also to FIGS. 22-24, pitch motions (as represented by arrows 944) of the example manipulator assembly 900 will now be further described. The pitch motions of the manipulator device 900 entail curvilinear translational movements of the pod coupling 940 along the pitch arc 942 as depicted by arrows 944. In these figures, the arm 920 is shown transparently so that mechanisms internal to the arm 920 can be visualized.

In the depicted embodiment, the arcuate path 942 is defined by the combination of a first, fixed arcuate segment 922 and a second, movable arcuate segment 926. The movable arcuate segment 926 is movably coupled to the fixed arcuate segment 922 so that the movable segment 926 telescopes distally with reference to fixed segment 922. As shown, movable segment 926 is positioned and translates inside fixed segment 922, and optionally movable segment 926 is positioned and translates outside fixed segment 922. Such a telescoping arrangement offers advantages. For example, as shown in FIGS. 22 and 23, the telescopic arrangement of the arcuate segments 922 and 926 allows the overall length of the manipulator assembly 900 to be shorter as compared to an arm that has only a fixed arcuate portion with the same pitch range of motion). Having a shorter overall length can advantageously reduce the potential for collisions between manipulator assemblies (e.g., when two or more manipulator assemblies are used during a surgery as depicted in FIG. 4). Additionally, shortening overall length of the manipulator assembly 900 allows for enhanced patient access by clinical personnel and more flexibility in manipulator positioning in relation to the patient.

As described above for arm 820, arm 920 includes one or more pitch-adjustment motors 930 which bi-directionally, rotatably drive a leadscrew 936. A nut 938 is threadably coupled to the leadscrew 936 and is rotationally constrained such that rotations of the leadscrew 936 result in translational movements of the nut 938. The first end 952 of the link 950 is pivotably coupled to the nut 938. The second end 954 of the link 950 is pivotably coupled to the pod 940. Hence, as the nut 938 translates along the longitudinal axis of the lead screw 936, the second end 954 of the link 950 drives translation of the pod coupling 940 to follow the curvilinear path of the pitch arc 942. The sequence of FIGS. 22-24 illustrate pod coupling 940 translating along pitch arc 942, as well as movable segment 926 telescoping in relation to fixed segment 922.

As shown in FIG. 22, in a full surgical tool pitch-forward configuration the pod coupling 940 is located at its proximal end range of motion limit in relation to the movable arcuate segment 926, and the movable arcuate segment 926 is located at its proximal end range of motion limit in relation to the fixed arcuate segment 922. As the link 950 is driven distally in relation to the arm 920, the pod coupling 940 first begins to translate distally along a curvilinear path defined by the movable arcuate segment 926 while the movable arcuate segment 926 remains stationary in relation to the fixed arcuate segment 922. As shown in FIG. 23, in the configuration in which the pod coupling 940 has reached its distal range of motion limit in relation to the movable arcuate segment 926, the movable arcuate segment 926 begins to move distally in relation to the fixed arcuate segment 922. As the link 950 is driven still farther distally in relation to the arm 920, the movable arcuate segment 926, with the pod coupling 940 remaining at its distal range of motion limit in relation to the movable arcuate segment 926, translates distally along a curvilinear path defined by the fixed arcuate segment 922 until the movable arcuate segment 926 its distal range of motion limit in relation to the fixed arcuate segment 922, as depicted in FIG. 24.

A proximal retraction of the movable arcuate segment 926 and the pod coupling 940 to their proximal range of motion limits (e.g., moving from the configuration of FIG. 24 toward the configuration of FIG. 23, and further toward the configuration of FIG. 22) can take place as a reversal of the above-described sequence of distal movements. In some embodiments, the movable arcuate segment 926 is spring-biased towards its proximal end range of motion limit in relation to the fixed arcuate segment 922. Accordingly, movable segment 926 remains at its proximal range of motion limit as link 950 drives pod coupling 940 through the proximal portion of pod coupling's full pitch range of motion (e.g., FIG. 22). As link 950 drives pod coupling 940 beyond its distal range of motion limit within movable link 926 (e.g., FIG. 23), the pitch-adjustment actuator overcomes the spring bias, and movable link 926 and pod coupling 940 together begin to translate distally along fixed segment 922 to move pod coupling 940 through the distal portion of pod coupling 940's full pitch range of motion (e.g., FIG. 24).

During retraction, the link 950 is retracted proximally (starting from the configuration of FIG. 24), and the spring bias keeps the movable arcuate segment 926 against pod coupling 940. When the movable arcuate segment 926 reaches its proximal range of motion limit in relation to the fixed arcuate segment 922, then the pod coupling 940 will begin to translate proximally along the curvilinear path defined by the movable arcuate segment 926 until the pod coupling 940 reaches its proximal range of motion in relation to the movable arcuate segment 926.

In some embodiments, the extension and retraction movements of the movable arcuate segment 926 in relation to the fixed arcuate segment 922 can be motorized. A separate motorized linear actuator drives movable arcuate segment through its arcuate range of motions. In some embodiments, other telescoping or telescoping actuator arrangements may be used to control the movable segment's position with reference to the fixed segment as the pod coupling is moved distally and proximally with reference to the fixed and movable segments.

The bearing arrangements used to movably couple the pod coupling 940 with the movable arcuate segment 926, and to movably couple the movable arcuate segment 926 with the fixed arcuate segment 922, are analogous to the bearing arrangements used to movably couple the pod coupling 840 with the arm 820 as described above in reference to the manipulator assembly 800 (see, e.g., FIGS. 18-20). That is, a first group of multiple bearings (e.g., four bearings) are affixed to pod coupling 940 and travel in the arcuate grooves defined in movable segment 926, and a second group of multiple bearings (e.g., four bearings) are affixed to movable segment 926 and travel in the arcuate grooves defined in fixed segment 922. Likewise, a first group of lateral bearings (e.g., four bearings) are affixed to pod coupling 940 and bear against one or more inner planar surfaces of movable segment 926, and a second group of lateral bearings (e.g., four) are affixed to movable segment 926 and bear against one or more inner planar surfaces of fixed segment 922. Such bearing arrangements can advantageously provide structural stability and rigidity of the pod coupling 940 in relation to the movable arcuate segment 926, and of the movable arcuate segment 926 in relation to the fixed arcuate segment 922 (as described above in reference to the bearing arrangements between the pod coupling 840 and the arm 820).

As described above for manipulator assembly 820, other arcuate mechanisms that include two or more arcuate grooves, or one or more arcuate rails, or one or more arcuate rods, etc. may be used in other embodiments.

In the depicted embodiment, the manipulator device 900 can adjust through a range of about 80° of pitch motion. That is, the pod coupling 940 can translate in relation to the arm 920 along the pitch arc 942 through about 80° of travel. In some embodiments, the manipulator device 900 is configured to facilitate a range of pitch motion of about 50° to about 70°, about 60° to about 80°, about 70° to about 90°, about 80° to about 100°, about 90° to about 110°, or about 100° to about 120°.

As described previously, the nut 938 is constrained from rotating. One mechanism by which the nut 938 is so constrained also advantageously helps prevent or reduce the exertion of undesirable lateral forces to the leadscrew 936. In particular, the arm 920 defines two elongate linear channels that extend parallel to the leadscrew 936 on opposite sides of the leadscrew 936. Two bearings 953 are movably engaged within the two elongate linear channels 939. The two bearings 953 can be rotatably coupled with the nut 938 or with the first end 952 of the link 950. This arrangement will transfer forces from the link 950 (that would otherwise be exerted laterally to the leadscrew 936) to the elongate linear channels of the arm 920 via the bearings 953.

Referring again to FIG. 21, it can be seen that the depicted manipulator 1100 does not explicitly show a pod roll motor analogous to motor 846 shown for example in FIG. 8 above. Although not explicitly shown, an analogous pod roll motor may be implemented in some embodiments. And in some embodiments with both fixed and telescoping pitch arcs, an internal pod roll motor may be used. For example, when pod 1000 is mounted to pod coupling 940 (or pod 700 to pod coupling 840), the internal pod roll motor rolls the pod around insertion axis.

In some embodiments, the manipulator device 900 may include electronic sensors and the like for various advantageous purposes. For example, encoders may be coupled to the drive trains of the motorized pitch, roll, and/or yaw adjustment mechanisms. In some embodiments, position sensors may be used that can positively identify the locations of the movable components of the manipulator device 900.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

We claim:

1. A teleoperated manipulator system comprising:
a mounting base;
an arm comprising a distal pitch arc portion, a pitch-adjustment actuator, and a movable link, the arm being coupled to the mounting base to rotate around a yaw axis, the movable link having a proximal end and a distal end, the proximal end of the movable link being coupled to the pitch-adjustment actuator, the pitch arc portion defining a pitch arc having a center;
a tool actuator assembly coupling coupled to translate on a curvilinear path in the pitch arc portion of the arm, the distal end of the movable link of the arm being coupled to the tool actuator assembly coupling; and
a tool actuator assembly coupled to the tool actuator assembly coupling, a long axis of the tool actuator assembly defining a tool insertion axis;
wherein the yaw axis, the center of the pitch arc, and the tool insertion axis are coincident and define a remote center of motion of the manipulator system; and
wherein the tool actuator assembly coupling comprises a roll-adjustment actuator coupled to drive the tool actuator assembly to rotate around the tool insertion axis.

2. The teleoperated manipulator system of claim 1, wherein:
the distal pitch arc portion of the arm comprises a fixed arcuate segment and a movable arcuate segment coupled to the fixed arcuate segment, the fixed arcuate segment and the movable arcuate segment together defining the pitch arc;
the movable arcuate segment is coupled to translate on a curvilinear path in the fixed arcuate segment; and
the tool actuator assembly coupling is coupled to translate on a curvilinear path in the movable arcuate segment.

3. The teleoperated manipulator system of claim 2, wherein:
the arm comprises a spring positioned to bias the movable arcuate segment to a proximal end of a range of motion of the movable arcuate segment on the curvilinear path in the fixed arcuate segment.

4. The teleoperated manipulator system of claim 1, wherein:
the pitch-adjustment actuator comprises a linear actuator.

5. The teleoperated manipulator system of claim 1, wherein:
the arm includes a projection extending into the mounting base to define a roll joint having an axis of rotation; and
the axis of rotation of the roll joint defines the yaw axis.

6. The teleoperated manipulator system of claim 1, wherein:
the mounting base comprises a sector gear;
the arm comprises a yaw-adjustment motor and a pinion gear coupled to the motor, the pinion gear being engaged with the sector gear of the mounting base; and
the yaw-adjustment motor drives the arm about the yaw axis.

7. The teleoperated manipulator system of claim 1, wherein:

the arm comprises a yaw-adjustment motor having an axis of rotation parallel to and offset from the yaw axis; and the yaw-adjustment motor drives the arm about the yaw axis.

8. The teleoperated manipulator system of claim 1, wherein:

the mounting base is configured to releasably couple to a setup arm configured to hold the mounting base stationary in space.

9. The teleoperated manipulator system of claim 1, wherein:

the pitch adjustment actuator comprises a plurality of ganged motors.

10. The teleoperated manipulator system of claim 1, wherein:

the tool actuator assembly coupling comprises a first gear coupled to the roll-adjustment actuator;

the tool actuator assembly comprises a second gear coupled to the first gear; and rotation of the first gear drives the tool actuator assembly to rotate around the tool insertion axis.

11. The teleoperated manipulator system of claim 1, wherein:

the tool actuator assembly is interchangeable with a second tool actuator assembly.

12. The teleoperated manipulator system of claim 1, wherein:

the tool actuator assembly is configured to translate a tool along the insertion axis.

13. The teleoperated manipulator system of claim 1, wherein:

the tool actuator assembly is configured to actuate a movable component of a tool mounted in the tool actuator assembly.

14. The teleoperated manipulator system of claim 1, further comprising:

a cannula releasably coupled to the tool actuator assembly coupling opposite the tool actuator assembly.

* * * * *

UNITED STATES PATENT AND TRADEMARK OFFICE
CERTIFICATE OF CORRECTION

PATENT NO. : 11,135,027 B2
APPLICATION NO. : 16/326851
DATED : October 5, 2021
INVENTOR(S) : Ryan Charles Abbott, John Ryan Steger and Daniel H. Gomez It is certified that error appears in the above-identified patent and that said Letters Patent is hereby corrected as shown below:

On the Title Page

Column 2, (57) ABSTRACT, Line 7, please replace "amounting" with -- a mounting --.

Signed and Sealed this
Third Day of May, 2022

Katherine Kelly Vidal
*Director of the United States Patent and Trademark Office*